United States Patent
Real García et al.

(10) Patent No.: US 11,365,227 B2
(45) Date of Patent: Jun. 21, 2022

(54) PEPTIDE AND PHARMACEUTICAL COMPOSITIONS OF SAME FOR USE AS AN ANTIMICROBIAL AND IN CANCER TREATMENT

(71) Applicant: UNIVERSITAT DE VALÈNCIA, Valencia (ES)

(72) Inventors: María Dolores Real García, Valencia (ES); Carolina Rausell Segarra, Valencia (ES); Inmaculada García Robles, Valencia (ES); María Benito Jardón, Valencia (ES); Aída Robles Fort, Valencia (ES)

(73) Assignee: UNIVERSITAT DE VALÈNCIA

(*) Notice: Subject to any disclaimer, the term of this patent is extended or adjusted under 35 U.S.C. 154(b) by 0 days.

(21) Appl. No.: 16/955,370

(22) PCT Filed: Dec. 21, 2018

(86) PCT No.: PCT/ES2018/070824
§ 371 (c)(1),
(2) Date: Jun. 18, 2020

(87) PCT Pub. No.: WO2019/122489
PCT Pub. Date: Jun. 27, 2019

(65) Prior Publication Data
US 2021/0002339 A1 Jan. 7, 2021

(30) Foreign Application Priority Data
Dec. 22, 2017 (ES) .............. ES201731455

(51) Int. Cl.
| | | |
|---|---|---|
| C07K 14/47 | (2006.01) | |
| A61K 38/00 | (2006.01) | |
| A61P 31/04 | (2006.01) | |
| A61P 35/00 | (2006.01) | |
| A61K 45/06 | (2006.01) | |

(52) U.S. Cl.
CPC .......... C07K 14/4723 (2013.01); A61P 31/04 (2018.01); A61P 35/00 (2018.01); A61K 38/00 (2013.01); A61K 45/06 (2013.01); A61K 2300/00 (2013.01)

(58) Field of Classification Search
CPC .............................. C07K 14/4723; A61K 38/00
See application file for complete search history.

(56) References Cited

U.S. PATENT DOCUMENTS

2016/0122391 A1* 5/2016 Lapidot .............. C07K 14/4723
514/19.8

OTHER PUBLICATIONS

Tribolium Genome Sequencing Consortium, 2008, The genome of the model beetle and pest *Tribolium castaneum*, 452(24): 949-955.*

Rajamuthiah et al., 2015, A Defensin from the Model Beetle *Tribolium castaneum* Acts Synergistically with Telavancin and Daptomycin against Multidrug Resistant *Staphylococcus aureus*, PLoS ONE, 10(6): e0128576 (14 pages).*
Tonk et al., 2015, Tribolium castaneum defensins are primarily active against Gram-positive bacteria, Journal of Invertebrate Pathology, 132: 208-215.*
Altincicek et al., 2008, Beetle immunity: Identification of the immune-inducible genes from the model insect *Tribolium castaneum*, Developmental and Comparative immunology, 32: 585-595.*
Contreras et al., 2015, Tribolium castaneum immune defense genes are differentially expressed in response to Bacillus thuringiensis toxins sharing common receptor molecules and exhibiting disparate toxicity, Developmental and Comparative Immunology, 50: 139-145. See Figure 2.*
Braunecker et al., 2004, The effects of molecular weight and porosity on the degradation and drug release from polyglycolide, International Journal of Pharmaceutics, 282: 19-34.*
International Search Report, International Patent Application No. PCT/ES2018/070824, dated Apr. 17, 2019.
Tonk, M. et al.; "Tribolium castaneum defensins are primarily active against Gram-positive bacteria," Journal of Invertebrate Pathology, Feb. 11, 2015, vol. 132, pp. 208-215; Abstract Only.
Rajamuthiah R. et al.; "A Defensin from the Model Beetle *Tribolium castaneum* Acts Synergistically with Telavancin and Daptomycin against Multidrug Resistant *Staphylococcus aureus*," PLoS ONE, Oct. 6, 2015, vol. 10, No. 6, pp. 1-14.
Contreras E. et al.; "Tribolium castaneum immune defense genes are differentially expressed in response to Bacillus thuringiensis toxins sharing common receptor molecules and exhibiting disparate toxicity," Developmental and Comparative Immunology, Dec. 2, 2015, vol. 50, pp. 139-145 Abstract Only.
Iwasaki, T. et al.; "Selective cancer cell cytotoxicity of enantiomeric 9-mer peptides derived from beetle defensins depends on negatively charged phosphatidylserine on the cell surface," Peptides, Dec. 30, 2008, vol. 30, pp. 660-668.
Figueira, T.N. et al.; "Challenging metastatic breast cancer with the natural defensin PcD1," Nanoscale, Oct. 2017, vol. 9, No. 43, pp. 16887-16899.
Extended European Search Report for EP 18890389.2 dated Sep. 23, 2021.
B. Altincicek et al., Beetle immunity: Identification of immune-inducible genes from the model insect *Tribolium castaneum*, Develpmental and Comparative Immunology, 2007, 32(5), 585-95.
Database UniProt, 2010, Subname: Full=Defensin-like Protein {ECO:0000313 EMBL:EFA10744.1}.
D. Gaspar, et al., From antimicrobial to anticancer peptides. A review, Frontiers in Microbiology, 2013, 4, 294, DOI=10.3389/fmicb.2013.00294.

* cited by examiner

*Primary Examiner* — Amber D Steele
(74) *Attorney, Agent, or Firm* — Tristan A. Fuierer; Casimir Jones, S.C.

(57) ABSTRACT

The present invention relates to a peptide derived from the defensin-3 from the red flour beetle *Tribolium castaneum*, to pharmaceutical compositions containing same, and to the use thereof as an antimicrobial in the treatment of infections caused by gram-positive bacteria, gram-negative bacteria and fungi. The invention also relates to the use of the peptide and pharmaceutical compositions containing same, in the treatment of cancer, particularly breast cancer. The compound described is a peptide derived from defensin-3 from the red flour beetle *T. castaneum*.

21 Claims, 20 Drawing Sheets

Specification includes a Sequence Listing.

A

B

C

D

A

B

A

B

C

D

A

B

C)

D)

A)

B)

SEQUENCE LISTING

<160> NUMBER OF SEQ ID NOS: 2

<210> SEQ ID NO 1
<211> LENGTH: 31
<212> TYPE: PRT
<213> ORGANISM: Artificial Sequence
<220> FEATURE:
<223> OTHER INFORMATION: Synthetic Construct

<400> SEQUENCE: 1

Lys Val Asn His Ala Ala Cys Ala Ala His Cys Leu Leu Lys Arg Lys
1               5                   10                  15

Arg Gly Gly Tyr Cys Asn Lys Arg Arg Ile Cys Val Cys Arg Asn
            20                  25                  30

```
<210> SEQ ID NO 2
<211> LENGTH: 29
<212> TYPE: PRT
<213> ORGANISM: Artificial Sequence
<220> FEATURE:
<223> OTHER INFORMATION: Synthetic Construct

<400> SEQUENCE: 2

Val Asn His Ala Ala Cys Ala Ala His Cys Leu Leu Lys Arg Lys Arg
1               5                   10                  15

Gly Gly Tyr Cys Asn Lys Arg Arg Ile Cys Val Cys Arg
            20                  25
```

PEPTIDE AND PHARMACEUTICAL COMPOSITIONS OF SAME FOR USE AS AN ANTIMICROBIAL AND IN CANCER TREATMENT

CROSS-REFERENCE TO RELATED APPLICATIONS

This application is filed under the provisions of 35 U.S.C. § 371 and claims the priority of International Patent Application No. PCT/ES2018/070824, filed on 21 Dec. 2018 entitled "PEPTIDE AND PHARMACEUTICAL COMPOSITIONS OF SAME FOR USE AS AN ANTIMICROBIAL AND IN CANCER TREATMENT" in the name of Maria Dolores REAL GARCIA, et al., which claims priority to Spanish Patent Application No. P201731455 filed on 22 Dec. 2017, both of which are hereby incorporated by reference herein in their entirety.

FIELD OF THE INVENTION

The present invention relates to compounds and pharmaceutical compositions for use as an antimicrobial agent in the treatment of infections caused by Gram+ or Gram− bacteria and fungi. The present invention also relates to compounds and pharmaceutical compositions for use in the treatment of cancer, specifically breast cancer. The compound disclosed is a peptide derived from the defensin 3 of the red flour beetle, *Tribolium castaneum*.

BACKGROUND OF THE INVENTION

Antimicrobial peptides (AMPs) are promising candidates for new antibiotic agents, as they have a different mechanism of action than conventional antibiotics. They are excellent agents for counteracting the development of antibiotic resistance. The rate at which antimicrobial peptides promote cellular death is an additional factor contributing to the reduction of the likelihood of developing resistance. In addition, these peptides can also act synergistically with conventional antibiotics, enhancing and improving their therapeutic activity.

Antimicrobial peptides have a small size, generally present positive charges and a ratio of hydrophilic to hydrophobic residues that confers amphipathic characteristics on them. The combination of the hydrophobicity and cationic nature allows them to interact electrostatically with microbial membranes, which generally have lipid-rich anionic surfaces.

These peptides form part of the innate immunity of all living organisms, from bacteria to vertebrates, as well as fungi, insects and plants, but not to the same extent. While in invertebrates they constitute the principal defense tool of their immune system, in vertebrates they also modulate adaptive immunity through chemotactic activity, proinflammatory signalling and aid in the healing process.

*Tribolium castaneum*, the red flour beetle, is an insect responsible for infesting stored foods and is a model organism for research into developmental biology, evolution, immunity, etc.

Document Contreras et al., 2015 discloses the antimicrobial effect of fragments of the defensins of the coleopteran *T. castaneum* (Tc) against *Bacillus thuringiensis* (Bt). In the presence of the entomopathogenic toxins Cry3Aa and Cry3Ba of this bacterium, the larvae of the insect develop an immune response inducing the expression of the defensins 2 and 3 of *T. castaneum* (TcDef2 and TcDef3). The document discloses that TcDef3-pep, a peptide fragment of TcDef2 with 29 amino acids has antimicrobial activity against *Escherichia coli, Staphylococcus aureus* and *Candida albicans*, where particularly remarkable is the susceptibility of *S. aureus*. The peptide TcDef3-pep corresponds to the sequence identified as SEQ ID NO: 2 of the present invention.

Document Rajamuthiah et al., 2015 discloses antimicrobial peptides with activity against *S. aureus*. The authors disclose a peptide obtained from *T. castaneum* (XM_968482, coding for peptide XP_973575.3) with antibacterial activity. Although the authors of this article refer to defensin 1, the amino acid sequence shown in FIG. 1A corresponds to defensin 3 of *T. castaneum*.

Document Tonk et al., 2015 discloses the antimicrobial activity of defensins of *T. castaneum* against Gram+bacteria. The three defensins (Def1, Def2 and Def3) have activity against *Micrococcus luteus* and *B. thuringiensis*, while only Def1 and Def2 have activity against *Staphylococcus epidermis*. The authors test the activity of the defensins against *S. aureus*, observing the lack of antimicrobial activity against this organism (FIG. 2 in said document).

The five types of cancer with the highest mortality are lung, liver, colorectal, stomach and breast cancer. Specifically, breast cancer has the highest incidence in Europe (458,718 cases, 13% of total cases) and the second highest incidence worldwide (1.7 million cases, 12% of total cases), and occupies the third and fifth place regarding mortality, respectively.

Breast carcinomas present neoplasms with a wide heterogeneity that have led to the need for different classification systems: histological, molecular markers, and functional. The most widely used classification from a clinical standpoint is that related to molecular markers, which includes oestrogen receptors (ER), progesterone receptors (PR), and the human epidermal growth factor 2 (HER2). According to the presence or absence of these markers, breast tumours can be distributed into four basic subtypes: ER or PR positive and HER2 negative ([ER+|PR+] HER2−), ER or PR positive and HER 2 positive ([ER+|PR+] HER2+), ER and PR negative and HER2 positive ([ER−|PR−] HER2+), also known as HER2 positive, and lastly ER and PR negative and HER2 negative ([ER−|PR−] HER2−) also known as triple negative breast cancer (TNBC) which is the most aggressive form with the worst prognosis.

The treatment of breast cancer requires a multidisciplinary approach, personalised for each patient, that combines surgery, radiotherapy, chemotherapy and hormone therapy. Triple negative breast cancer presents several additional problems, as it does not respond to hormonal therapies since it lacks receptors, it is associated with a risk of metastasis four times greater than other breast tumours, and the peak risk of recurrence is observed between the first and third year, with most deaths occurring in the first five years. Chemotherapy is the only treatment that improves outcomes in TNBC, but its high cytotoxicity for healthy cells and the appearance of chemoresistances has led to research into other treatment options, such as molecule targeted therapies. Unfortunately, most of these therapies are associated with the acquisition of resistance by tumour cells, which limits the efficacy of the treatment. An interesting improvement would be the development of new drugs against triple negative breast cancer that selectively kill tumour cells or limit their proliferation, and which are not affected by the known resistance mechanisms.

DETAILED DESCRIPTION OF THE INVENTION

Within the context of products with antimicrobial activity, the problem in the state of the art is to find peptides derived from the defensin 3 of *T. castaneum* with an improved antimicrobial activity with respect to the peptides derived from the defensin 3 of *T. castaneum* described in the state of the art.

The present invention solves said problem providing a peptide and a pharmaceutical composition thereof which have not been described in the state of the art. This new peptide and pharmaceutical composition thereof have an unexpected effect and show increased activity against *S. aureus* with respect to other peptides derived from the defensin 3 of *T. castaneum* with antimicrobial activity disclosed in the state of the art.

The peptide with sequence SEQ ID NO: 1 has 31 amino acids, an additional amino acid at each terminus compared to the peptide TcDef3-pep disclosed in Contreras et al., 2015, this being the structural difference between the two peptides.

The peptide disclosed in Rajamuthiah et al., 2015, named Tca1, presents activity against *S. aureus*, but its sequence has 44 amino acids instead of the 31 amino acids of SEQ ID NO: 1.

In the context of products with activity against cancer, the problem of the state of the art consists in providing compounds effective for use in the treatment of cancer.

The present invention solves said problem providing a peptide that comprises the sequence SEQ ID NO: 1 and a pharmaceutical composition thereof, effective for use in the treatment of cancer. This new use in the treatment of cancer has not been described previously in the state of the art.

In the present specification the term "PaSK" makes reference to the peptide identified by the sequence SEQ ID NO: 1. Therefore, in the present specification the terms and expressions "PaSK", "peptide consisting of the sequence SEQ ID NO: 1" and "sequence SEQ ID NO: 1", are interchangeable.

In the present specification the term "TcDef3-pep" makes reference to the peptide identified by the sequence SEQ ID NO: 2. Therefore, in the present specification the terms and expressions "TcDef3-pep", "peptide consisting of the sequence SEQ ID NO: 2" and "sequence SEQ ID NO: 2", are interchangeable.

Peptide and Pharmaceutical Composition Comprising the Peptide

The present invention provides a peptide consisting of the sequence SEQ ID NO: 1.

In one embodiment, the present invention provides a pharmaceutical composition consisting of the sequence SEQ ID NO: 1 and at least one pharmaceutically acceptable excipient or carrier.

In one embodiment, the carrier is selected from the group consisting of organic nanoparticles, selected from the group consisting of: lipids, nanoemulsions, polymer mycelles, SCK nanoparticles, liposomes, nanogels, hydrogels, lipoplexes, polyplexes; polymers selected from the group consisting of: albumin, cellulose, chitosan, alginate, gelatin, poly-ε-caprolactone (PCL), hydroxyethyl starch (HES; MEA), polyglycolate (PGA), poly-(lactic-co-glycolid), polylactide (PLA), poly(d,l-lactide-co-glycolide) (PLGA), polyethyleneglycol (PEG), N-(2-hydroxypropyl) metacrylamide (poly(HPMA); PHPMA) and dextrane; dendrimers, selected from the group consisting of: polyether-hydroxylamine (PEHAM), polyamidoamine (PAMAM), polyesteramine, polypropyleneamine and polyglycerol; nanofibers, selected from the group consisting of: carbon nanotubes, nanofibers of poly(d,l-actide-co-glycolide) (PLGA), of polyethyleneglycol (PEG), of chitosan, of poly(vinyl alcohol) (PVA), of polylactide (PLA), of polyethylene oxide and of poly-ε-caprolactone (PCL); and inorganic nanoparticles, selected from the group consisting of: gold nanoparticles, metal oxide nanoparticles, titanium oxide nanoparticles, platinum oxide nanoparticles, superparamagnetic iron oxide nanoparticles (SPIO-NPs), diamond-based nanoparticles and QD nanoparticles.

In the present specification the term "nanoemulsions" makes reference to heterogeneous mixtures of two immiscible liquids with an emulsifier that stabilises the scattered drops.

In the present specification the term "polymer micelles" refers to amphiphilic copolymer chains self-assembled in an aqueous medium which present a hydrophobic nucleus surrounded by a hydrophilic crown. The polymer micelles include polyion complex (PIC) and polymer-metal complex micelles.

The acronym "SCK" refers to "shell cross-linked knedel-like". In the present specification the term "SCK nanoparticles" makes reference to amphiphilic copolymer chains self-assembled in polymer micelles, in which there is a selective cross linking in the outer shell.

In the present specification, the term "lipoplexes" makes reference to complexes formed by nucleic acids (DNA/RNA) and cationic lipids. Including PEGylated lipoplexes.

In the present specification, the term "polyplexes" makes reference to complexes formed by nucleic acids (DNA/RNA) and polymers. Including PEGylated polyplexes.

In the present specification, the term "carbon nanotubes" makes reference to cylindrical graphite sheets with a single or multiple wall.

The acronym "SPIO-NPs" refers to "superparamagnetic iron oxide nanoparticles".

The acronym "QD" refers to "quantum dots". In the present specification, the term "QD nanoparticles" makes reference to semiconducting inorganic nanoparticles, widely used as fluorophores in imaging techniques.

In one embodiment, the pharmaceutical composition comprises an effective amount of the peptide consisting in the sequence SEQ ID NO: 1.

For the purposes of the present invention, an effective amount is defined as the amount of compound that provides an objectively identifiable improvement in the condition of the patient, as recognised by a skilled observer, and where said patient is treated with a pharmaceutical composition comprising said amount of compound.

For the purposes of the present invention, pharmaceutically acceptable excipients are inert ingredients such as, but not limited to: cosolvents, surfactant agents, oils, wetting agents, emollients, preservatives, stabilisers and antioxidants. Said excipient or vehicle can be a diluent, for example. The pharmaceutical composition can be in crystalline, powder, granular, compacted solid, liquid, solution, suspension, elixir, syrup, emulsion, cream, gel, drop, mist, vapour or pulverised form. Conventional techniques can be used to prepare the pharmaceutical composition. For example, the pharmaceutical composition can be included in a capsule, tablet, pill, oblong pill, blister, envelope, syringe, cartridge, spray or other container.

The pharmaceutical composition of the invention can be administered by itself, or in combination with other active principles.

The pharmaceutical composition of the invention can be administered to a subject in various ways, depending on whether the treatment is local or systemic, and depending on the area to treat. Thus, for example, the pharmaceutical composition of the invention can be administered to a subject by ocular, vaginal, rectal, intranasal, oral routes, by inhalation or parenterally, whether intradermal, subcutaneous, intramuscular, intraperitoneal, intrarectal, intraarterial, intralymphatic, intravenous, intrathecal, intraocular, intracranial or intratracheal, routes. Parenteral administration, if used, is generally performed by injection. The solutions for injection can be prepared in various ways, such as liquid solutions or suspensions, solid forms suitable for dissolving or being placed in suspension before injection, or as emulsions. Other forms of parenteral administration use prolonged or sustained release systems to obtain a constant dose. Preparations for parenteral administration include aqueous or non-aqueous sterile solutions, suspensions, and emulsions, and can also contain buffers and diluent or other additives. Examples of non-aqueous solvents are: propyleneglycol, polyethyleneglycol, vegetable oils such as olive oils and organic esters for injection, such as ethyl oleate. Examples of aqueous solvents are: water, aqueous solutions of, emulsions or suspensions, which include saline solution and buffer. Examples of parenteral vehicles are: sodium chloride solution, Ringer's dextrose, sodium chloride and dextrose, etc. Preservatives and other additives can also be present, such as antimicrobial agents, antioxidants, chelating agents, inert gases, etc. Formulations for topical administration can include creams, lotions, gels, drops, suppositories, aerosols, liquids and powders. Certain conventional pharmaceutical carriers, aqueous bases, oleous bases, thickeners, etc. may also be necessary. The compositions for oral administration may include powders or granules, suspensions or solutions in water or non-aqueous medium, capsules or tablets. It may be desirable to include thickening agents, aromas, diluents, emulsifiers, dispersants, etc.

The pharmaceutical composition of the invention can be administrated in single or multiple doses.

In one embodiment, the pharmaceutical composition also comprises an antibiotic agent.

In one embodiment, said antibiotic agent is selected from the group consisting of fusidic acid, arsphenamine, clindamycin, chloramphenicol, ethambutol, fosfomycin, furazolidone, isoniazid, lincomycin, linezolid, metronidazol, mupirocin, nitrofurantoin, pirazinamid, platensimycin, quinupristin, rifampicin and tinidazol or an antibiotic of the class selected from: aminoglucosides, ansamycins, carbacefem, carbapenem, cephalosporins, glycopeptides, macrolides, monobactamics, penicillins, polypeptides, quinolones, sulfonamides and tetracyclins.

Peptide or Pharmaceutical Composition for Use as a Medicament and as an Antimicrobial Agent In one embodiment, the present invention provides a peptide consisting of the sequence SEQ ID NO: 1 or the pharmaceutical composition for use as a medicament.

In one embodiment, the present invention relates to the peptide or the pharmaceutical composition for use as an antimicrobial medicament.

In a preferred embodiment, the present invention relates to the peptide consisting of the SEQ ID NO: 1 or to the pharmaceutical composition comprising same, for use as an antimicrobial medicament in the treatment of infections caused by Gram+ bacteria, Gram− bacteria and fungi.

In a preferred embodiment, said Gram+ bacterium is *S. aureus*.

In a preferred embodiment, said Gram− bacterium is *E. coli*.

In a preferred embodiment, said fungus is *C. albicans*.

Peptide or Pharmaceutical Composition for Use in the Treatment of Cancer

In one embodiment, the present invention provides a peptide comprising the sequence SEQ ID NO: 1 or a pharmaceutical composition comprising said peptide and at least one pharmaceutically acceptable excipient or carrier, for use in the treatment of cancer.

In one embodiment, the pharmaceutical composition comprises an effective amount of the peptide comprising the sequence SEQ ID NO: 1.

Pharmaceutically acceptable excipients are inert ingredients such as, but not limited to: cosolvents, surfactant agents, oils, wetting agents, emollients, preservatives, stabilisers and antioxidants. Said excipient or vehicle can be a diluent, for example. The pharmaceutical composition can be in crystalline, powder, granular, compacted solid, liquid, solution, suspension, elixir, syrup, emulsion, cream, gel, drop, mist, vapour or pulverised form. Conventional techniques can be used to prepare the pharmaceutical composition. For example, the pharmaceutical composition can be included in: a capsule, tablet, pill, oblong pill, blister, envelope, syringe, cartridge, spray or other container.

The pharmaceutical composition can be administered by itself or in combination with other active principles.

The pharmaceutical composition can be administered to a subject in different ways, depending on whether the treatment is local or systemic, and depending on the area to treat. Thus, for example, the pharmaceutical composition can be administered to a subject ocularly, vaginally, rectally, intranasally, orally, by inhalation or parenterally, whether intradermically, subcutaneously, intramuscularly, intraperitoneally, intrarrectally, intraarterially, intralymphaticaly, intravenously, intrathecally, intraocularly, intracranially and intratracheally. Parenteral administration, if used, is generally performed by injection. The solutions for injection can be prepared in various ways, such as liquid solutions or suspensions, solid forms suitable for dissolving or being placed in suspension before injection, or as emulsions. Other forms of parenteral administration use prolonged or sustained release systems to obtain a constant dose. Preparations for parenteral administration include aqueous or non-aqueous sterile solutions, suspensions and emulsions, and can also contain buffers and diluent or other additives. Examples of non-aqueous solvents are: propyleneglycol, polyethyleneglycol, vegetable oils such as olive oils and organic esters for injection, such as ethyl oleate. Examples of aqueous solvents are: water, aqueous solutions of, emulsions or suspensions, which include saline solution and buffer. Examples of parenteral vehicles are: sodium chloride solution, Ringer's dextrose, sodium chloride and dextrose, etc. Preservatives and other additives can also be present, such as antimicrobial agents, antioxidants, chelating agents, inert gases, etc. Formulations for topical administration can include creams, lotions, gels, drops, suppositories, aerosols, liquids and powders. Certain conventional pharmaceutical carriers, aqueous bases, oleous bases, thickeners, etc. may also be necessary. The compositions for oral administration may include powders or granules, suspensions or solutions in water or non-aqueous medium, capsules or tablets. It may be desirable to include thickening agents, aromas, diluents, emulsifiers, dispersants, etc.

The pharmaceutical composition can be administered in single or multiple doses.

In a specific embodiment, the present invention provides a peptide that consists in the sequence SEQ ID NO: 1 or a pharmaceutical composition comprising the peptide that consists in the sequence SEQ ID NO: 1 and at least one pharmaceutically acceptable excipient or carrier, for use in the treatment of cancer.

In one embodiment, the cancer is selected from the group consisting of breast cancer, anti-HER2 therapy resistant breast cancer, breast carcinoma, breast adenocarcinoma, gastric carcinoma, gastric adenocarcinoma, colon carcinoma, colon adenocarcinoma, pancreatic carcinoma, pancreatic adenocarcinoma, renal cell carcinoma, clear-cell renal cell carcinoma, ovarian carcinoma, ovarian adenocarcinoma, ovarian carcinoma, endometrial carcinoma, uterine cervix carcinoma, pulmonary carcinoma, pulmonary adenocarcinoma, non-microcytic lung cancer, small-cell lung cancer, thyroid carcinoma, metastasic papillary thyroid carcinoma, thyroid follicular carcinoma, vesical carcinoma, transitional cell carcinoma of the bladder, prostate gland carcinoma, central nervous system glyal lineage cancer (glyoma), sarcomas, fibrosarcoma, malign fibrous histiocytoma, human Edwing's sarcoma, endometrial stroma sarcoma, osteosarcoma, rabdomiosarcoma, melanoma, embryonary cancers, neuroblastoma, medulloblastoma, retinoblastoma, nephroblastoma, hepatoblastoma, haematological cancers, B-cell or T-cell leukaemia, non-Hodgkin's lymphoma, B-cell or T-cell non-Hodgkin's lymphoma, Burkitt's lymphoma, Hodgkin's lymphoma, leukaemias, B-cell or T-cell lymphoma, and multiple myeloma.

In a preferred embodiment, the cancer is breast cancer.

In a more preferred embodiment, the breast cancer is triple-negative breast cancer.

The peptide of the present invention interacts efficiently with heterogeneous tumour cells, allowing them to exercise their intrinsic anticarcinogenic activity or in synergy with other therapeutic agents, and presents a lower likelihood of developing resistances than other therapeutic agents.

In one embodiment, the peptide or pharmaceutical composition is used to treat cancer in combination with treatment with a chemotherapeutic agent, treatment with an immunotherapeutic agent, or with a radiotherapeutic treatment.

In one embodiment, said chemotherapeutic agent is selected from the group consisting of: anastrozol, capecitabine, carboplatin, oxaliplatin, ciclophosphamide, cisplatin, docetaxel, doxorubicin, eribulin, fulvestrant, imiquimod, letrozol, paclitaxel, romidepsin, triciribine, exemestane, 5-fluorouracyl and gemcitabine.

In one embodiment, said immunotherapeutic agent is selected from the group consisting of: dovitinib, ipilimumab, lapatinib, margetuximab, neratinib, nivolumab, olaparib, palbociclib, pembrolizumab, pertuzumab, ruxolitinib, trastuzumab and veliparib.

In one embodiment of the pharmaceutical composition for use in the treatment of cancer, said carrier is selected from the group consisting of organic nanoparticles, selected from the group consisting of: lipids, nanoemulsions, polymer mycelles, SCK nanoparticles, liposomes, nanogels, hydrogels, lipoplexes, polyplexes; polymers selected from the group consisting of: albumin, cellulose, chitosan, alginate, gelatin, poly-ε-caprolactone (PCL), hydroxyethyl starch (HES; MEA), polyglycolate (PGA), poly-(lactic-co-glycolid), polylactide (PLA), poly(d,l-lactide-co-glycolide) (PLGA), polyethyleneglycol (PEG), N-(2-hydroxypropyl) metacrylamide (poly(HPMA); PHPMA) and dextrane; dendrimers, selected from the group consisting of: polyetherhydroxylamine (PEHAM), polyamidoamine (PAMAM), polyesteramine, polypropyleneamine and polyglycerol; nanofibers, selected from the group consisting of: carbon nanotubes, nanofibers of poly(d,l-actide-co-glycolide) (PLGA), of polyethyleneglycol (PEG), of chitosan, of poly (vinyl alcohol) (PVA), of polylactide (PLA), of polyethylene oxide and of poly-ε-caprolactone (PCL); and inorganic nanoparticles, selected from the group consisting of: gold nanoparticles, metal oxide nanoparticles, titanium oxide nanoparticles, platinum oxide nanoparticles, superparamagnetic iron oxide nanoparticles (SPIO-NPs), diamond-based nanoparticles and QD nanoparticles.

In one embodiment, the pharmaceutical composition for use in the treatment of cancer further comprises a chemotherapeutic agent or an immunotherapeutic agent.

In a preferred embodiment, the combination of the peptide and the chemotherapeutic agent or immunotherapeutic agent achieves an improved treatment of cancer compared to the individual administration of each member of said combination.

In one embodiment, said chemotherapeutic agent is selected from the group consisting of: anastrozol, capecitabine, carboplatin, oxaliplatin, ciclophosphamide, cisplatin, docetaxel, doxorubicin, eribulin, fulvestrant, imiquimod, letrozol, paclitaxel, romidepsin, triciribine, exemestane, 5-fluorouracyl and gemcitabine.

In one embodiment, said immunotherapeutic agent is selected from the group consisting of: dovitinib, ipilimumab, lapatinib, margetuximab, neratinib, nivolumab, olaparib, palbociclib, pembrolizumab, pertuzumab, ruxolitinib, trastuzumab and veliparib.

The results of Examples 3 and 4 show that PaSK (peptide consisting in the sequence SEQ ID NO: 1) inhibits tumour growth and proliferation, regulating the progress of the cell cycle, affecting the G1/S transition in triple-negative breast cancer cells. The p53 tumour suppression protein generally mediates the interruption of the cell cycle and apoptosis in response to genotoxic stress. MDA-MB-231 cells have specific mutations that make the p53 non-functional in them. Therefore, the inhibition of growth and proliferation of triple-negative breast cancer cells by PaSK not depending on p53 makes the peptide PaSK of great interest for therapeutic use in breast tumours in which p53 is often mutated.

Definitions

In the present specification, the term "cancer" can encompass all types of oncogenic and/or cancerous growth processes. In some embodiments the cancer includes primary tumours, as well as metastatic tissue or cells, tissues or organs with malignant transformations. In some embodiments the cancer encompasses all histopathologies and stages, such as stages of invasiveness/seriousness, of a cancer. In some embodiments the cancer includes recurrent and/or resistant cancer. The terms "cancer" and "tumour" may be used indistinctly.

Unless defined otherwise, all the technical and scientific terms used herein have the same meaning as those customarily understood by a person skilled in the field of the invention.

Methods and materials that are similar and equivalent to those described herein may be used in the practice of the present invention.

Throughout the description and the claims, the term "comprising", "that comprises" and their variants are of non-limiting nature and therefore should not exclude other technical features.

Throughout the description and claims, the term "consisting in" or "that consists in", particularly when related to biological sequences, means that the compounds of the invention are restricted in a precise manner to the fragment identified by the specified sequence.

DESCRIPTION OF EMBODIMENTS

Figure 1:
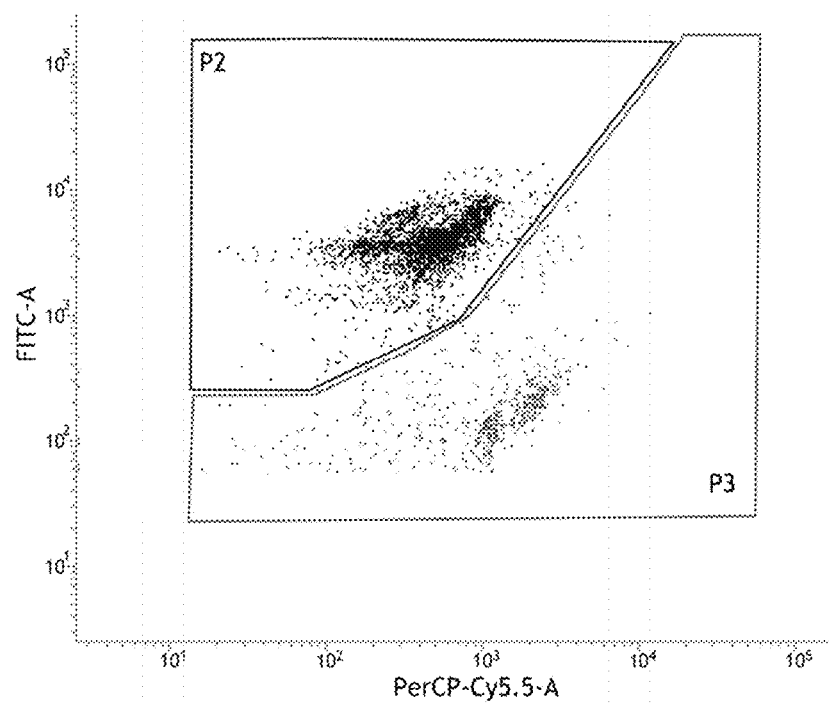
FIG. 1. Antimicrobial activity of the peptides hBD-3, TcDef3-pep and PaSK against *S. aureus*. Fluorescence graphs obtained at the flow cytometer windows of the negative control (A) and positive control hBD-3 (B). Fluorescence graphs obtained at the flow cytometer windows of the peptides TcDef3-pep (C) and PaSK (D). In the ordinate, FITC refers to fluorescein and indicates the cells that have incorporated SYBR green. In the abscissa, PerCP-Cy5.5-A refers to the proteins peridinin-chlorophyll and corresponds to the cells that have captured propidium iodide. Window P2 shows live cells and P3 shows dead cells.
Figure 1:
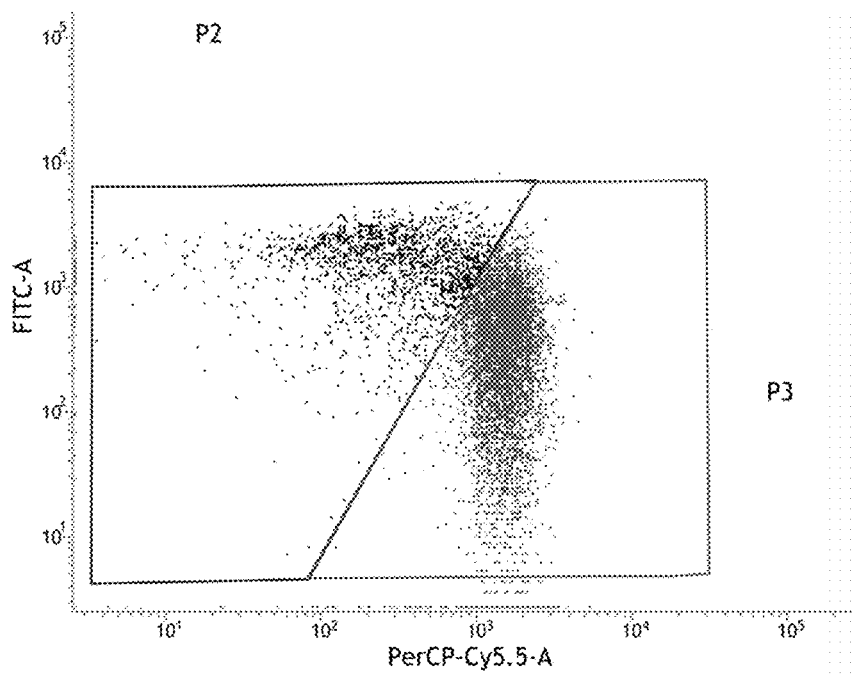
Figure 1:
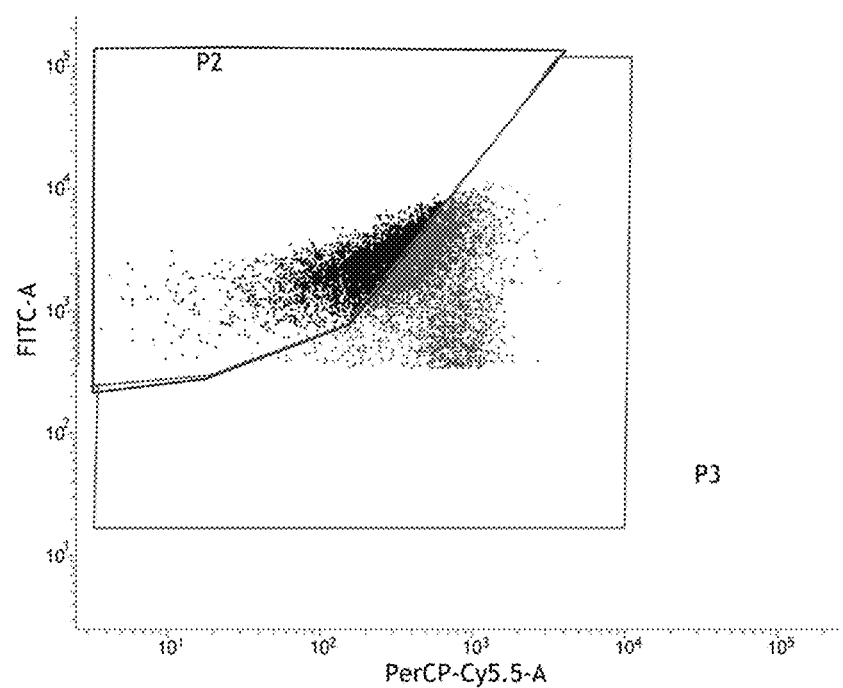
Figure 1:
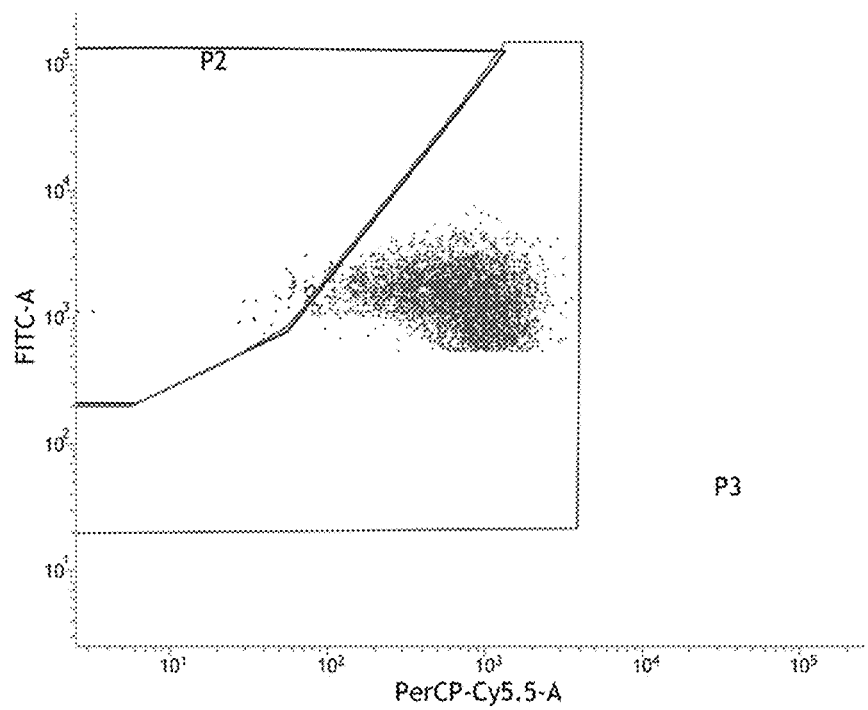

Materials and Methods
Peptides Used
The synthetic peptides used in this study were: TcDef3-pep and PaSK, fragments of the defensin 3 of *T. castaneum*, and the human defensin hBD-3 (PeptaNova).

Bacterial Strain of *Staphylococcus aureus* Subsp. *aureus*
The strain used was CECT 4013 of *S. aureus* subsp. *aureus*, publicly accessible deposited in the Spanish Type Culture Collection (CECT).

Human Mammary Gland Tumour Cell Line MDA-MB-231
The human mammary gland tumour cell line MDA-MB-231 was used, identified as ATCC® HTB-26™, cell line publicly accessible deposited in the American Type Culture Collection (ATCC). The cells were cultured in 75 cm² flasks supplemented with bovine foetal serum 10%, penicillin and streptomycin 1% and fungizone 0.1%, and maintained at 37° C. in an atmosphere containing 5% $CO_2$.

Preparation of the Samples
The MDA-MB-231 cells were cultured in dishes with 6 wells with a density of $5 \times 10^4$ cells per well, in which 200 µL or 400 µL of PaSK were added (final concentrations 100 µg/mL and 200 µg/mL) or the same volume of the medium (solvent used to dilute the peptide) in the corresponding controls. The cells were incubated at 37° C. for 72 h.

Flow Cytometry for *S. aureus* Cells
Starting from cells of *S. aureus* cultured overnight in a liquid medium LB (peptone 1%, yeast extract 0.5% and NaCl 1%) at 37° C. with stirring, aliquots were obtained in a new liquid medium and allowed to grow until reaching an optical density at 600 nm (OD600) of 0.5, optimum for detection in the flow cytometer. Aliquots were prepared with a concentration of $5 \times 10^6$ cfu/100 µL of *S. aureus* to which were added 10, 15, 20 and 25 µg/mL of PaSK, 25 µg/mL of TcDef3-pep and $H_2O$ (negative control), solvent used to dilute the peptides. The mixtures were incubated at 37° C. for 8 h and marked with the fluorochromes SYBR Green (Invitrogen) (25 µL of a SYBR Green 25× solution in $H_2O$) that stains all the cells and propidium iodide (Sigma) (10 µL of propidium iodide 1 mg/mL) that stains dead cells. Finally, the cell death caused by the peptides was analysed by flow cytometry with the equipment BD Facs Verse (Becton Dickinson), from the cell culture and flow cytometry section of the Central Services for Research Support of the University of Valencia. The experiments were performed in duplicate.

The flow cytometer forces cells to pass one by one through a needle, creating a thin line of liquid and detecting how the laser beam (argon emission laser at 488 nm, in the equipment used) interacts with the cells, depending on how the incident light is deviated and the fluorescence emitted by the excited fluorochromes. The results are presented as graphs obtained with the analysis program BD Facs suite v1.0.5.3841 (Becton Dickinson). Firstly, a control graph is obtained with the parameters FSC (Forward Scatter) and SSC (Side Scatter) to find all cellular events. These parameters provide the cell size and granularity, respectively. Then, a second graph is obtained with the parameters SSC and FITC (fluorescence parameter indicating the cells containing SYBR Green), to differentiate the cells from the other particles that may be present in the sample. Lastly, a third graph is obtained with the fluorescence parameters FITC and PerCPCy5.5 (indicating the cells stained with propidium iodide) to differentiate the cells that have been stained only by SYBR Green from those stained with propidium iodide, which will be those that have died.

Flow Cytometry for Human Mammary Gland Tumour Cells MDA-MB-231
To estimate cell viability, the cells of the cell line MDA-MB-231 were incubated with 0.5 µL of a 1:1000 dilution of the fluorochrome propidium iodide (PI) 1 mg/mL (Sigma-Aldrich), with which the dead cells were stained.

For the cell line analysis, the CycleTEST™ PLUS DNA Reagent Kit (Sigma-Aldrich) was used. Two washes were carried out using citrate buffer (containing sodium citrate, saccharose and dimethyl sulphoxide (DMSO)), centrifuging the samples in each one at 300×g for 5 min, and one final wash was performed in which the number of cells was adjusted to $5 \times 10^5$ and centrifuged at 400×g for 5 min, and then adding 250 µL of solution A (containing trypsin in a detergent buffer with spermine tetrahydrochloride), 200 µL of solution B (containing an inhibitor of trypsin and ribonuclease A, in a stabilising buffer of citrate with spermine tetrahydrochloride) and 200 µL of solution C (includes PI and the stabilising buffer with spermine tetrahydrochloride), leaving between the addition of each solution an interval of 10 min at room temperature and performing the last one, before filtering, in a cold chamber and in the dark. The analyses of cell death produced by the peptide and of the stage of cell cycle of the cells were performed with the equipment BD Facs Verse (Becton Dickinson). The cell cycle modelling was performed with the software Modfit LT, version 3.3.11. The experiments were performed in duplicate.

MTS Method

Cell viability was determined by the MTS method. The MDA-MB-231 cells cultured in plates with 96 wells at 37° C. in an atmosphere humidified with 10% $CO_2$ to a density of $5\times10^3$ cells/well were incubated with different concentrations of the peptide PaSK for 24 h. Then 20 µL were added of the solution MTS/PMS (3-(4,5-dimethylthiazol-2-yl)-5-(3-carboxymethoxyfenyl)-2-(4-sulphophenyl)-2H-tetrazole/phenazine methosulphate) to each well and after incubating for 2 h in the dark the absorbance at 490 nm was read in a plate reader. The percentage reduction in number of cells was calculated according to the formula $(1-E/C)\times 100$, where E is the absorbance of the cells treated with the peptide and C is the absorbance of the samples of the control cells.

Scanning Electron Microscopy of S. aureus Cells

The cells were prepared in the same way as for the flow cytometry technique and the same aliquots and treatments were performed. The samples were incubated at 37° C. for 1 h. The bacteria were fixed with Karnosky (2.5% paraformaldehyde and 0.5 glutaraldehyde) for 2 h at 4° C. After washing (centrifuging and eliminating the supernatant) they were fixed with 2% osmium tetraoxide for another 2 h, washed again and filtered with a 0.2 µm filter. The cells were then dehydrated in graded ethanol series (30°, 50°, 70°, 90°, 100°) for 10 min in each gradation. To carry out the critical point drying, the ethanol was replaced with liquid $CO_2$, the temperature was increased to accelerate evaporation and the pressure was lowered slowly to conserve the exact shape of the bacteria. Finally, shading with gold palladium was performed for 2 min observing the results in the equipment FEG-SEM HITACHI S4800 at 10 Kv.

Scanning Electron Microscopy of Human Mammary Gland Tumour Cells MDA-MB-231

The MDA-MB-231 cells, control or treated with 100 µg/mL of PaSK, were prepared as indicated in the section "Preparation of the samples". The cells were fixed with Karnosky (2.5% paraformaldehyde and 0.5% glutaraldehyde) for 2 h at 4° C. After washing (centrifuging and eliminating the supernatant) they were fixed with 2% osmium tetraoxide for another 2 h, washed again and filtered with a 0.2 µm filter. The cells were then dehydrated in graded ethanol series (30°, 50°, 70°, 90°, 100°) for 10 min in each gradation. To carry out the critical point drying, the ethanol was replaced with liquid $CO_2$, the temperature was increased to accelerate evaporation and the pressure was lowered slowly to conserve the exact shape of the cells. Finally, shading with gold palladium was performed for 2 min observing the results in the equipment FEG-SEM HITACHI S4800 at 10 Kv.

Transmission Electron Microscopy of S. aureus Cells and Human Mammary Gland Tumour Cells MDA-MB-231

The samples were prepared in the same way as for scanning electron microscopy, except for the series of graded dehydration with ethanol, in which only the 90° grade was reached. Then the samples were included in resin in 4 steps: ethanol 96°—resin LR-White 2:1 (20 h), ethanol 100°—resin 2:1 (20 h), ethanol 100°—resin 1:2 (20 h) and 100% resin (24 h at 60° C.). After the samples were included in the resin the block was prepared for ultrathin cuts of 60 nm in the equipment Leica UC6 Ultracut Microtome. Finally, the cuts were contrasted with lead and the results were observed in the equipment TEM JEOL-JEM1010 at 70 kV.

Example 1. Analysis of Antimicrobial Activity of the Peptide PaSK Against S. aureus In this example the antimicrobial activity of the peptide PaSK was compared to the antimicrobial activity of the peptide TcDef3-pep. The antimicrobial activity of the peptide TcDef3-pep against S. aureus has been described in Contreras et al., 2015.

The antimicrobial activity of the peptide PaSK was determined by flow cytometry. Said technique is based on light scattering by the cells and the use of fluorochromes to discriminate between live and dead cells. All cells are permeable to fluorochrome SYBR green, while only dead cells are permeable to propidium iodide, as the latter requires the bacterial membranes to be damaged in order to penetrate into the cells. Therefore, the use of these two fluorochromes provides a method for determining viable cells, quantifying the loss of cell viability from the increase in propidium iodide inside the dead cells.

After incubating the cells of strain CECT 4013 of S. aureus with 25 µg/mL of the peptides TcDef3-pep and PaSK, the percentage of dead cells was determined. As a positive control, human defensin hBD-3 at the same concentration was used, which has antimicrobial activity against several types of microorganisms, including S. aureus. FIGS. 1A-1D show the graphs corresponding to the fluorescence obtained in the windows of the flow cytometer. Window P2 shows live cells and window P3 shows dead cells.

Figure 2:
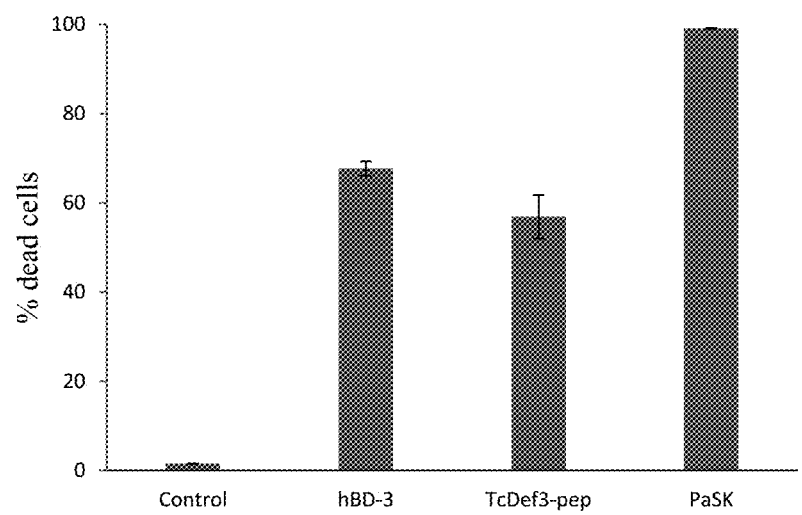
FIG. 2. Comparison of cytotoxicity among the peptides hBD-3, TcDef3-pep and PaSK against *S. aureus*. The activity was measured at a concentration of 25 μg/mL in 2 replicates. Shown is the activity for the negative control (control), positive control hBD-3, TcDef3-pep and PaSK. The graph shows the mean value for the two replicates with the corresponding standard deviations.

FIG. 2 shows the percentage of dead cells and the standard deviations (SD) of the two replicates analysed for the treatments with each peptide and for the control cells. The cytotoxicity of hBD-3 and TcDef3-pep was around 70% and 55%, respectively. However, the peptide PaSK presents a cell death percentage of almost 100%. The mortality turned out to be statistically significant with the two-tailed Student's t-test, with $p\leq0.05$ in the 3 peptides with respect to the negative control and in the peptide PaSK also with respect to TcDef3-pep and hBD-3 (FIG. 2).

Figure 3:
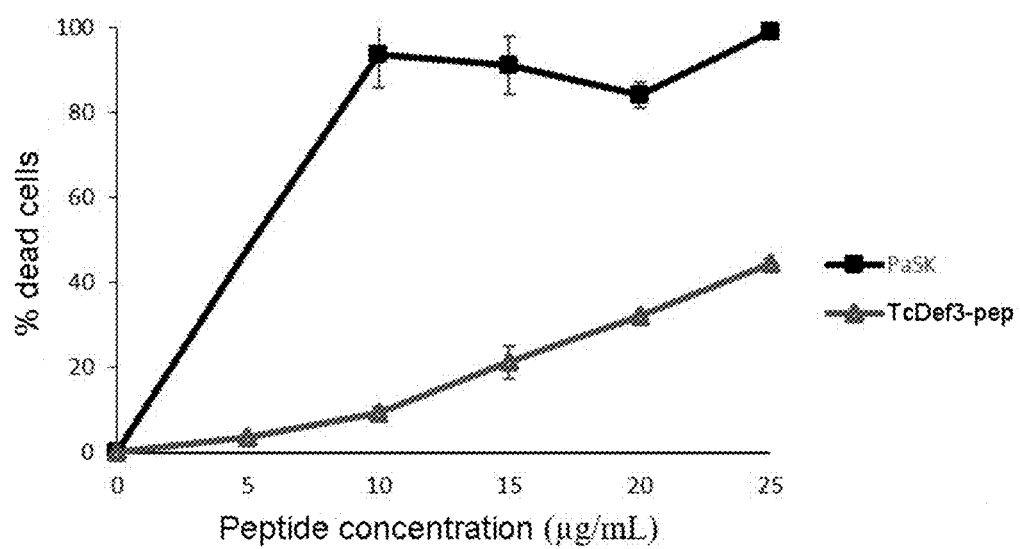
FIG. 3. Antimicrobial activity of the peptides TcDef3-pep and PaSK against *S. aureus*. The points represent the mean values of the two replicates with the corresponding standard deviations. Data for the peptide TcDef3-pep obtained from Contreras et al., 2015.

The antimicrobial activity was also analysed for the peptide PaSK at lower concentrations, 10, 15 and 20 µg/mL, in the same conditions as the previous experiments. FIG. 3 shows the percentage of cell death at said concentrations. It can be seen that at the concentration of 10 µg/mL in which the peptide TcDef3-pep showed a mortality percentage of 9.2% (Contreras et al., 2015), the peptide PaSK already shows cytotoxicity approaching 100%.

Figure 4:
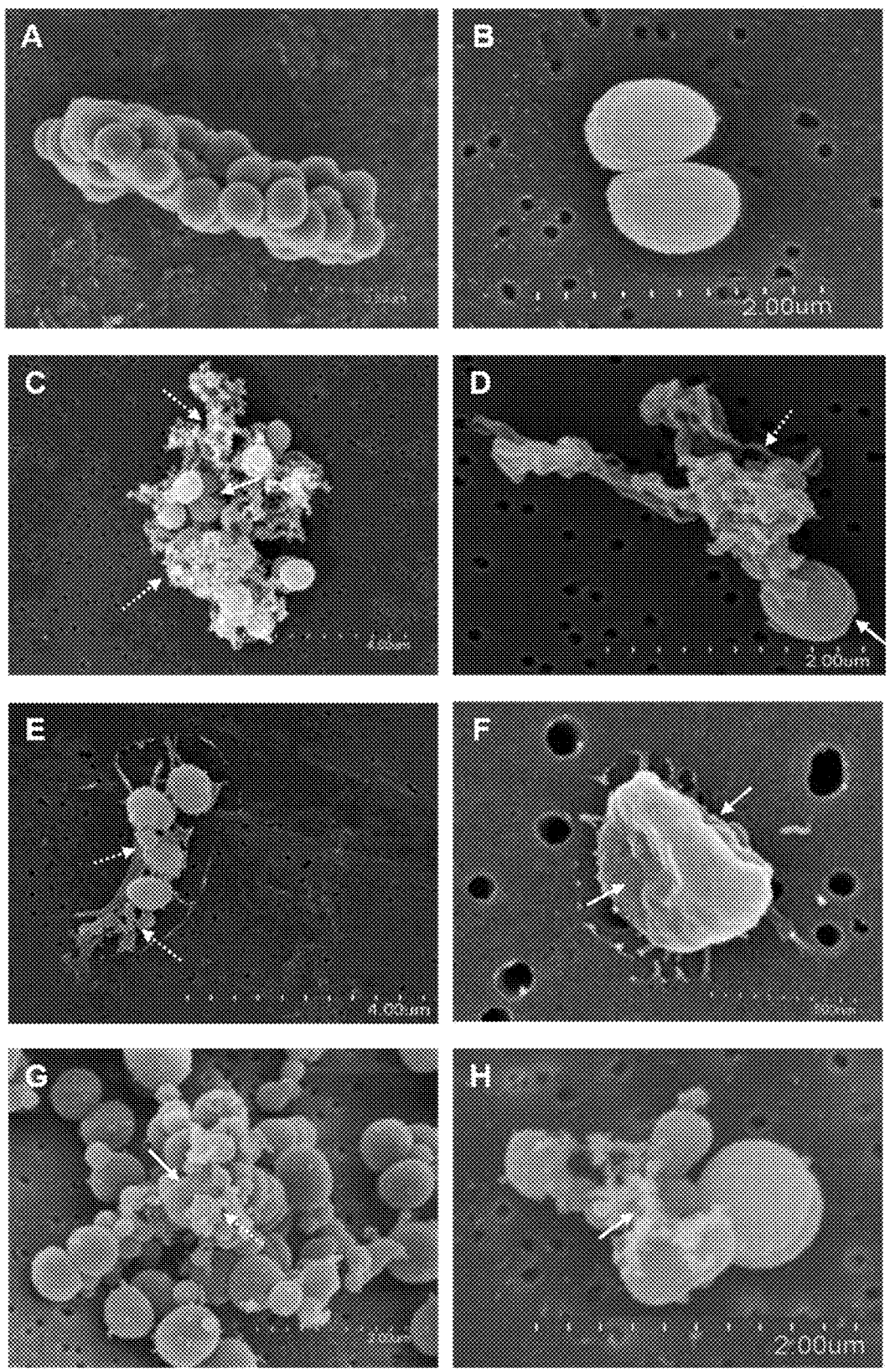
FIG. 4. Images of the damage caused by the peptides in *S. aureus* obtained by scanning electron microscopy. Cells non-treated with the peptides (A-B) and treated with hBD-3 (C-D), TcDef3-pep (E-F) and PaSK (G-H) at a concentration of 25 μg/mL for 1 hour are shown. Continuous arrows indicate ruptures and bulges in the membrane. Discontinuous arrows indicate cytoplasm debris. The number representing the scale is 3 μm (A), 2 μm (B), 4 μm (C), 2 μm (D), 4 μm (E), 500 nm (F), 2 μm (G) and 2 μm (H).

Example 2. Effect of the Peptides TcDef3-Pep and PaSK on the Morphology of S. aureus Scanning Electron Microscopy Scanning electron microscopy provides high-resolution images used to view the damage caused by the peptides to the bacterial membrane. The cells of S. aureus CECT 4013 were treated with the peptides hBD-3, TcDef3-pep and PaSK at a concentration of 25 µg/mL, for 1 h, and analysed using scanning electron microscopy (FIG. 4). In cells without treatment the circular and uniform form typical of S. aureus was observed, with the intact membrane, while in treated cells various types of morphological alterations can be seen. The images of cells treated with hBD-3 show structural damage and lysis of the membrane (continuous arrows), as well as important release of cytoplasm content (discontinuous arrows). In cells treated with the peptide TcDef3, bulges are observed in the bacterial membrane (continuous arrows) and some cytoplasm debris (discontinuous arrows), although less extensive than in the treatment with hBD-3. Lastly, cells treated with the peptide PaSK show irregular morphologies of the membrane (continuous arrow) and complete cell disintegration, with the ensuing release of cytoplasm debris (discontinuous arrow). With this treatment small circular structures are observed, smaller than the cells of *S. aureus*.

Figure 5:
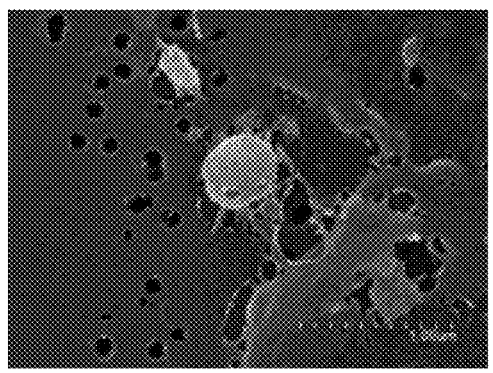
FIG. 5. Images obtained by scanning electron microscopy of the biofilm produced by cells of *S. aureus* treated with TcDef3-pep (A) and PaSK (B), at a concentration of 25 μg/mL for 1 h. The number represented in the scale is 1 μm (A, top image), 2 μm (A, central image), 4 μm (A, bottom image), 4 μm (B, top image), 2 μm (central image) and 3 μm (bottom image).
Figure 5:
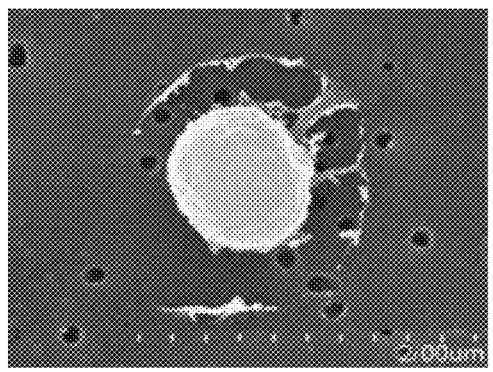
Figure 5:
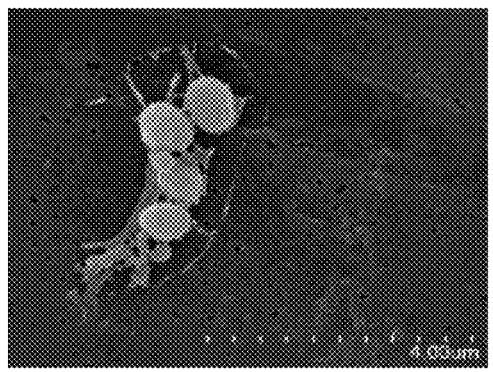
Figure 5:
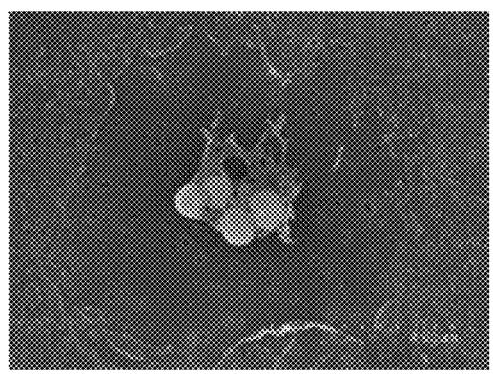
Figure 5:
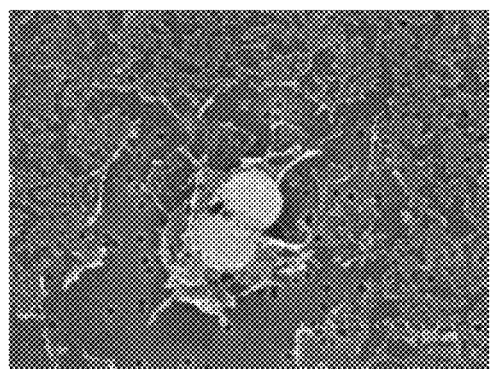
Figure 5:
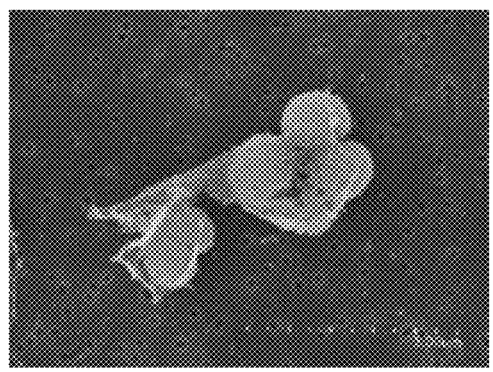

The images obtained by scanning electron microscopy of cells treated with the peptides show formation of a biofilm in the bacteria (FIG. 5). It was discarded that the formation of the exopolysaccharide was caused by lack of nutrients or other features of the culture medium, as the samples treated with hBD-3 (positive control) and those carrying $H_2O$ (negative control) grew with the same medium and did not form a biofilm (FIG. 4).

Transmission Electron Microscopy

Figure 6:
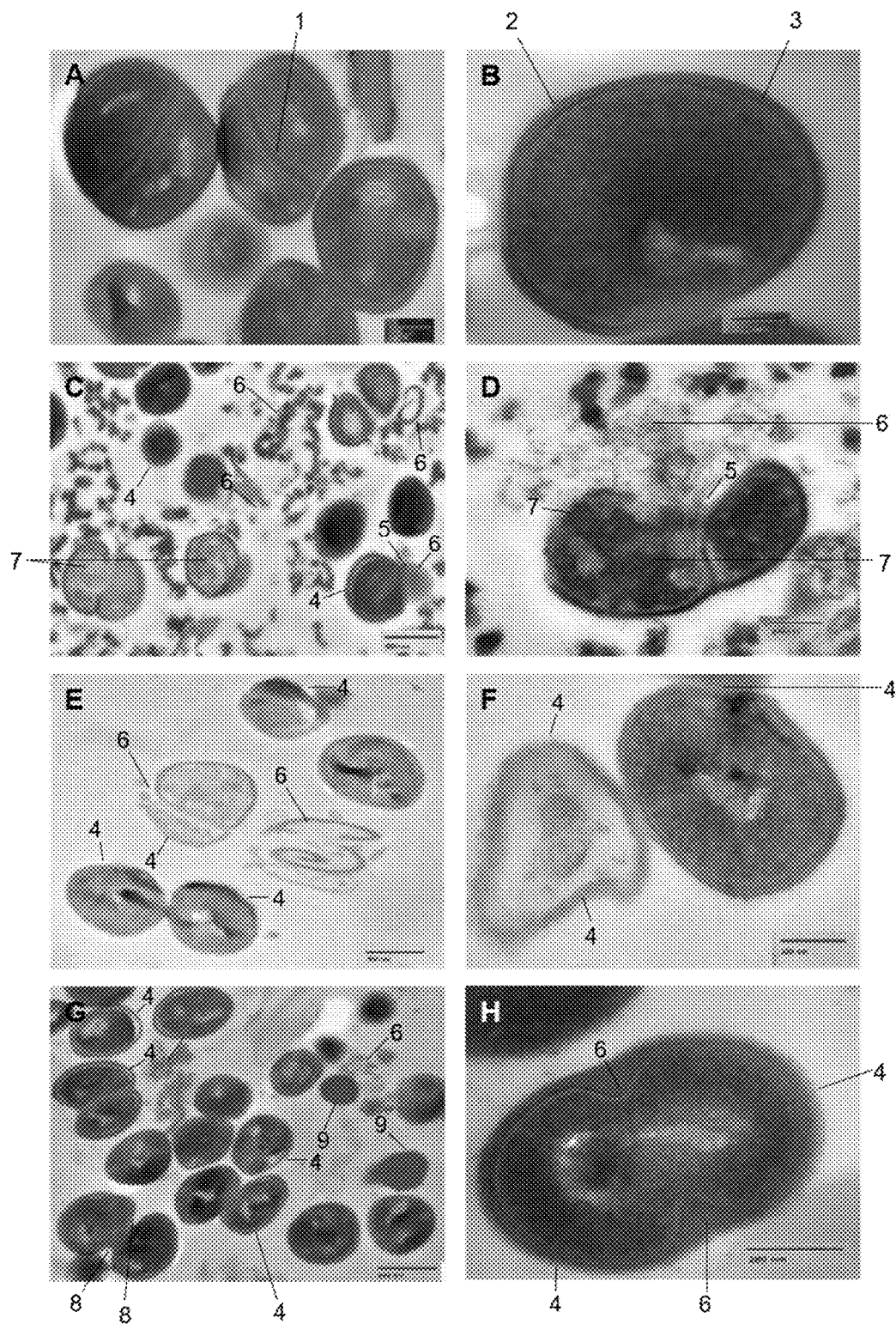
FIG. 6. Images of the damage caused by the peptides in *S. aureus* obtained by transmission electron microscopy. Cells non-treated with peptides (A-B) and treated with hBD-3 (C-D), TcDef3-pep (E-F) and PaSK (G-H) at a concentration of 25 μg/mL for 1 h are shown. Cytoplasm and cell wall debris (6), malformations, membrane shedding and thinning of the peptidoglycane (4), cell lysis (5), cytoplasm vacuolisation (7), malformation of the division septum (8) and some highly electrodense structures that appear only in cells treated with the peptide PaSK (9) are indicated. The number representing the scale is 200 nm (A), 100 nm (B), 600 nm (C), 200 nm (D), 400 nm (E), 200 nm (F), 600 nm (G) and 200 nm (H).
Figure 7:
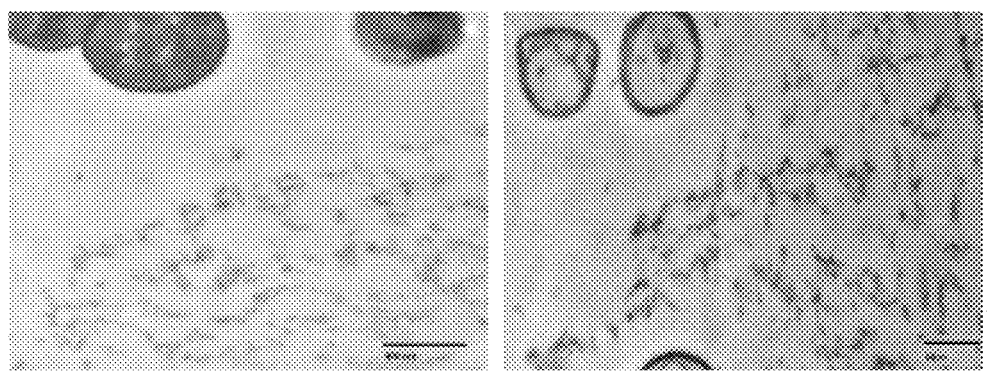
FIG. 7. Images obtained by transmission electron microscopy of the biofilm produced by cells of *S. aureus* treated with the peptides TcDef3-pep (A) and PaSK (B), at a concentration of 25 μg/mL for 1 h. The number representing the scale is 400 nm (A, left), 400 nm (A, right), 400 nm (B, left), 400 nm (B, right)
Figure 7:
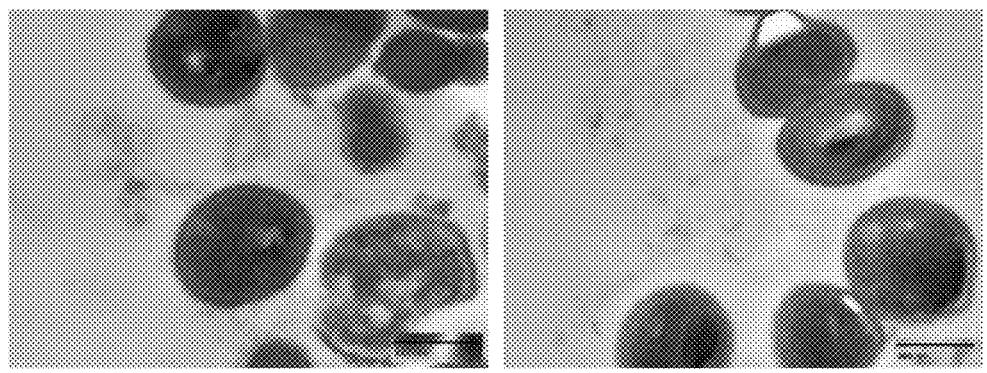

Transmission electron microscopy provides high-resolution images which were used to view the ultrastructural damage caused by the peptides inside the bacteria. The cells of *S. aureus* CECT 4013 were treated with the peptides hBD-3, TcDef3-pep and PaSK at a concentration of 25 μg/mL, for 1 h, and analysed using transmission electron microscopy (FIG. 6). In cells without treatment, an intact cytoplasm membrane (3) and peptidoglycane wall (2) were observed, typical of a Gram+ bacteria as *S. aureus*, as well as a division septum (1) without malformations, while in treated cells different types of alterations were observed. The images of the cells treated with hBD-3 show malformations (4) and lysis of the membrane (5), as well as an important release of cytoplasm content, detached wall remnants (6) and vacuolisation of the cytoplasm (7). Cells treated with the peptide TcDef3-pep show malformations and bulges in the bacterial membrane (4), some cytoplasm debris and detached wall remnants (6). Lastly, cells treated with the peptide PaSK show detachments, malformations and thinning of the membrane (4), escape of cytoplasm debris (6) and malformations and inhibition of the division septum (8). Small size circular structures (9) are observed. These structures show a different electrodensity from cells and lack a cytoplasm membrane and peptidoglycane wall. The biofilm formed by the cells treated with peptides was also observed in the images obtained by transmission electron microscopy (FIG. 7) and it was not observed in the cells treated with human defensin hBD-3 (FIG. 6).

Example 3. Analysis of Cytotoxic and Antiproliferative Activity of the Peptide PaSK The cytotoxic effect of the peptide PaSK has been studied in two cell lines of triple-negative breast cancer cells, one human (MDA-MB-231) and one mouse (4T1), and a line of normal mouse mammary epithelial cells (HC-11). To this end, a cell viability MTS assay was performed, based on the use of a compound derived from tetrazolium that is reduced in live cells to form a soluble coloured product.

Figure 8:
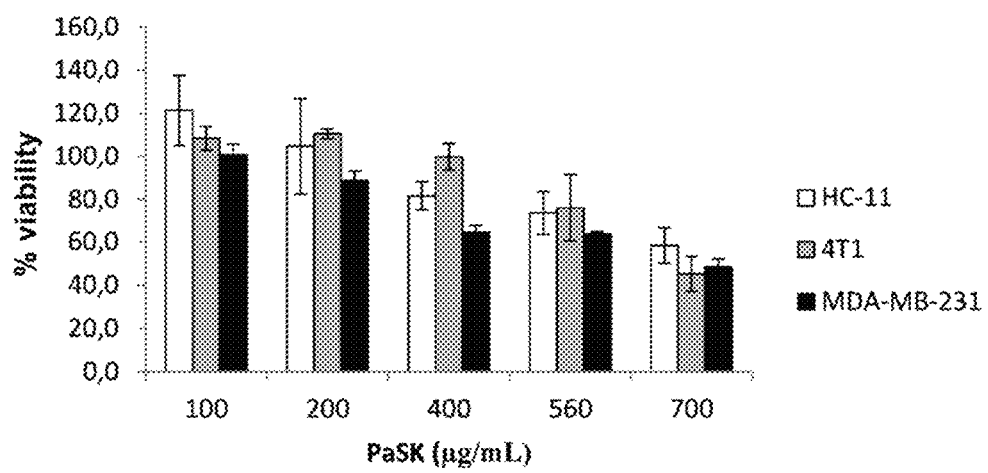
FIG. 8. Determination of the cytotoxic effect of the peptide PaSK in two cell lines of triple-negative breast cancer cells, one human (MDA-MB-231) and one mouse (4T1), and a line of normal mouse mammary epithelial cells (HC-11) by a MTS test. Results are shown for a 0.5% bovine foetal serum with 24 h incubation. The peptide PaSK causes a cell mortality of about 50% at concentrations of approximately 200 μM (700 μg/mL) in the three cases.

Various concentrations of peptide (5 μg/mL to 700 μg/mL) were tested at different times (3 h, 24 h and 48 h) and in the presence of different concentrations of bovine foetal serum in the test (0.5% and 10%), as it has been described that serum affects the activity of antimicrobial peptides. The results obtained showed that for a bovine foetal serum concentration in the test of 0.5% and 24 h incubation, the peptide PaSK presents cytotoxic activity that is dose dependent in the two cell lines of triple negative cancer cells studied, as well as in the line of normal mammary epithelial cells, causing a mortality in the cells of around 50% at concentrations of approximately 200 μM (700 μg/mL) in the three cases (FIG. 8). These data confirm that the peptide PaSK presents cytotoxic activity in mammalian cells at high concentrations. However, in a range of peptide concentrations of around 100 μM (400 μg/mL), PaSK resulted significantly more cytotoxic for human triple-negative breast cancer cells (MDA-MB-231).

A cell proliferation analysis was performed by flow cytometry for tumour cells marked with the fluorophore Oregon Green subsequently treated with a concentration of 50 μM (200 μg/mL) of the peptide PaSK or with $H_2O$ as control. This analysis allowed exploring the use of PaSK in a combined therapeutic approach. The combined use of therapeutic agents meant to inhibit tumour growth and maintenance and agents capable of stimulating the patient's immune response in the treatment of cancer is an alternative therapeutic approach to conventional approaches based only on cytotoxic agents for reducing the impact of the two main problems associated with the exclusive use of cytotoxic agents in cancer therapy: non-specific toxicity and the appearance of resistance.

Figure 9:
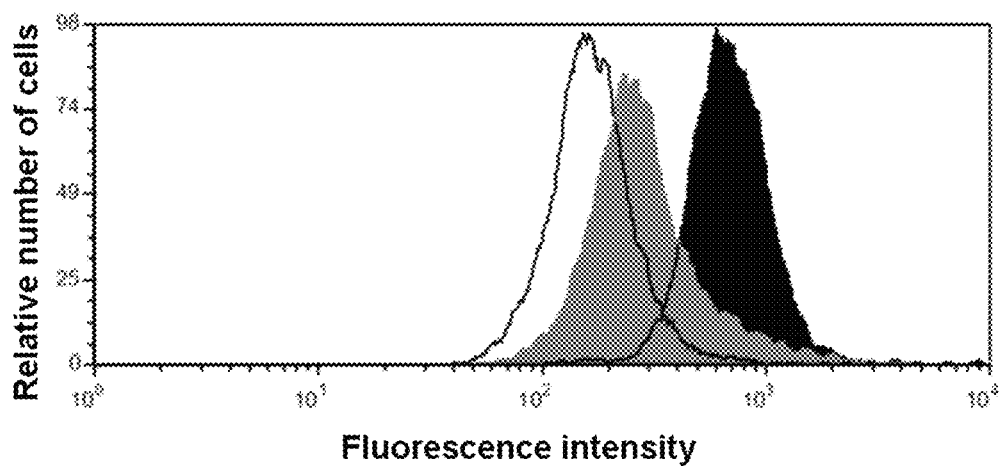
FIG. 9. The peptide PaSK inhibits cell proliferation in human triple-negative breast cancer cells (MDA-MB-231). The cells were incubated with Oregon Green. The cell proliferation analysis was performed by flow cytometry for tumour cells marked with Oregon Green fluorophore. The results of the non-proliferative control (peak with area in black colour), cells not treated with the peptide (peak with area in white colour) and cells treated with 50 μM (200 μg/mL) of the peptide PaSK (peak with area in grey colour) are shown.

The reagent Oregon Green is covalently bonded to free amine groups of cells, conferring on same a homogeneous fluorescence that is distributed among the daughter cells in each cell division. As the fluorescence intensity of the cells is approximately halved with each cell division, the final fluorescence intensity after treatment with the peptide and in non-treated control cells compared to the initial fluorescence intensity of the cells provides information on how many cell division cycles have occurred in each case. FIG. 9 shows the results obtained. Cells treated with the peptide PaSK show greater fluorescence intensity than non-treated cells, indicating that the peptide inhibits proliferation of human triple-negative breast cancer cells.

Example 4. Analysis of Cytotoxic and Antiproliferative Activity of the Peptide PaSK In this example, the cytotoxic and antiproliferative activity of the peptide PaSK is assessed by flow cytometry, performing an analysis of cell viability and an analysis of the cell cycle. After treatment of the tumour cells MDA-MB-231 with 200 μg/mL (cell viability experiments) and 100 μg/mL (analysis of cell cycle) of PaSK the percentage of viable cells was determined, as well as the stage of the cell cycle in which proliferation was stopped.

Figure 10:
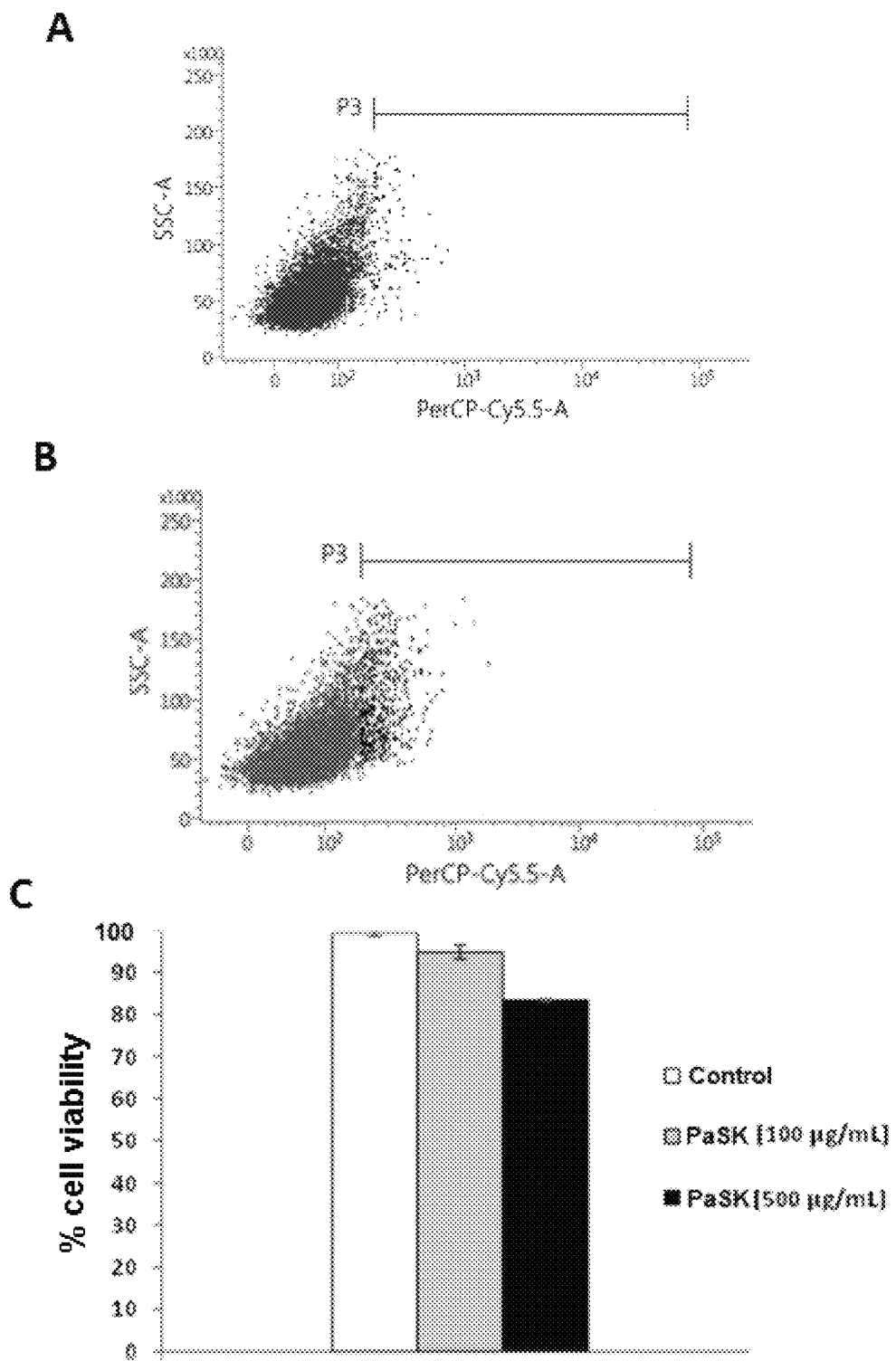
FIG. 10. Cytotoxic activity of the peptide PaSK against MDA-MB-231 tumour cells. Graphs of live and dead cells obtained in the flow cytometer, control (A) and treatment with PaSK (B). In the ordinate, SSC-A (Side Scatter) refers to the granularity of the cells in the selected population. In the abscissa, PerCP-Cy5.5-A refers to the Peridinin-chlorophyll proteins and corresponds to the cells that have captured propidium iodide. The activity was measured at a concentration of 200 μg/mL of PaSK in two replicates. Viability graph showing the means of the two replicates and their corresponding standard deviations (C).

FIGS. 10A and 10B show the graphs corresponding to cell viability in view of the fluorescence of propidium iodide (PI), shown in the graphs, obtained from the flow cytometry (region P3 corresponds to dead cells). In the control experiment (FIG. 10A) a cell viability of 98% was obtained, while in the treatment with PaSK (FIG. 10B) the cell viability was 93%.

FIG. 10C shows the percentage of live cells and the standard deviations (SD) of the two replicates analysed for the treatments with PaSK and for the control cells. The mortality percentage with peptide PaSK at a concentration of 200 μg/mL for MDA-MB-231 cells was around 5%, statistically significant with respect to the control.

Figure 11:
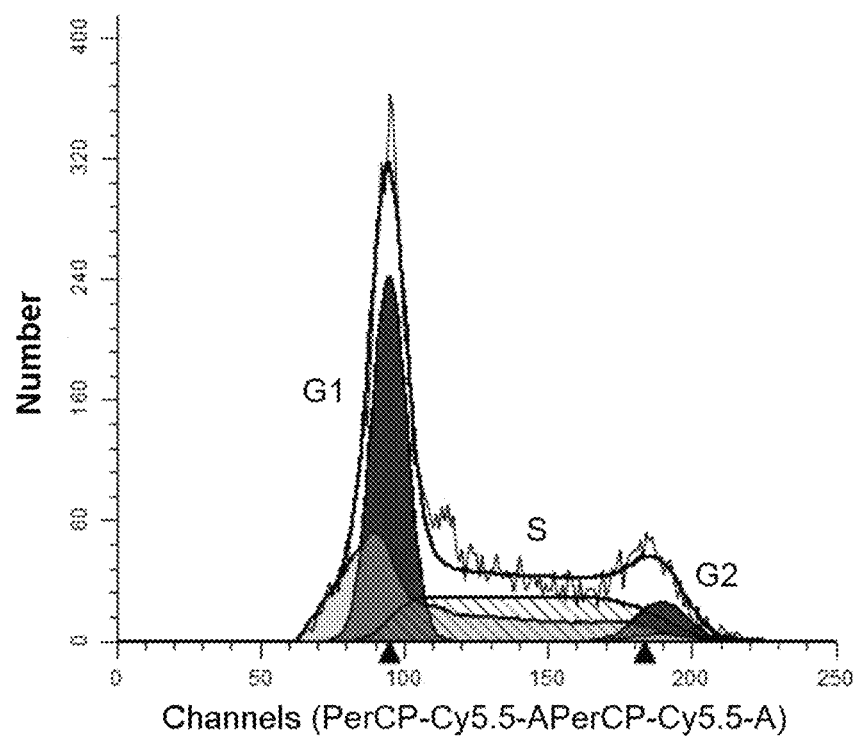
FIG. 11. Antiproliferative activity of the peptide PaSK against MDA-MB-231 tumour cells. Analysis of cell cycle progression using software ModFit LT, A) Control B) PaSK (100 μg/mL). The cell distribution was detected for the various stages of the cell cycle in 2 replicates. C) Graph of the percentage of cells observed in each stage of the cell cycle, showing the means of the two replicates and their corresponding standard deviations. The asterisk indicates statistically significant differences between treatments (Student's t-test, $p \leq 0.05$). D) Schematic of the cell cycle showing the stage affected by the action of the peptide PaSK.
Figure 11:
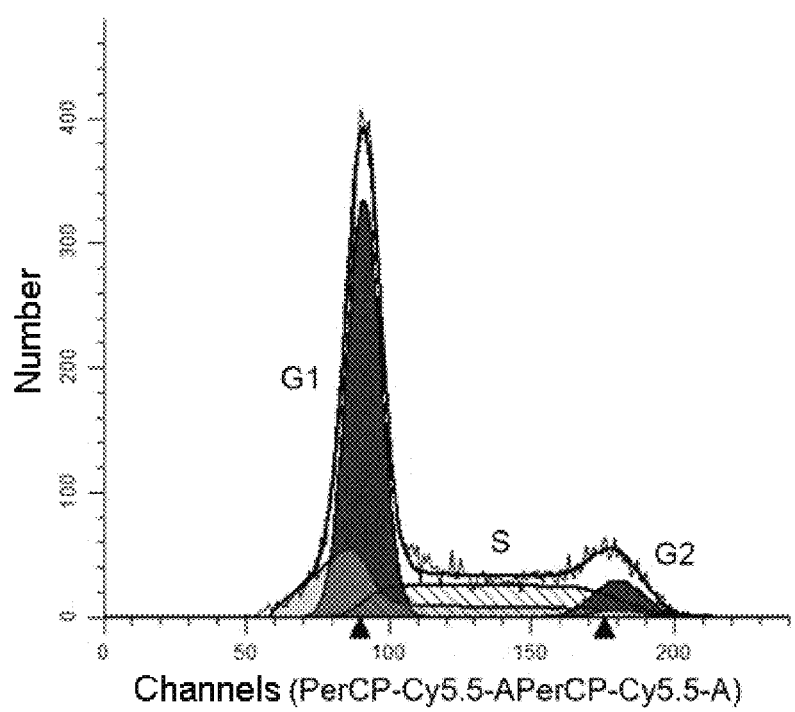
Figure 11:
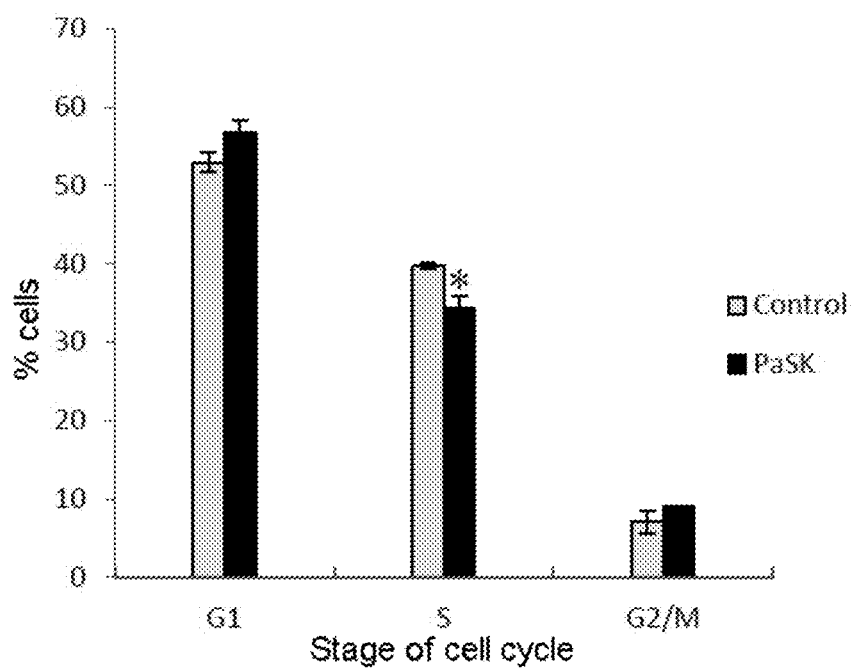
Figure 11:
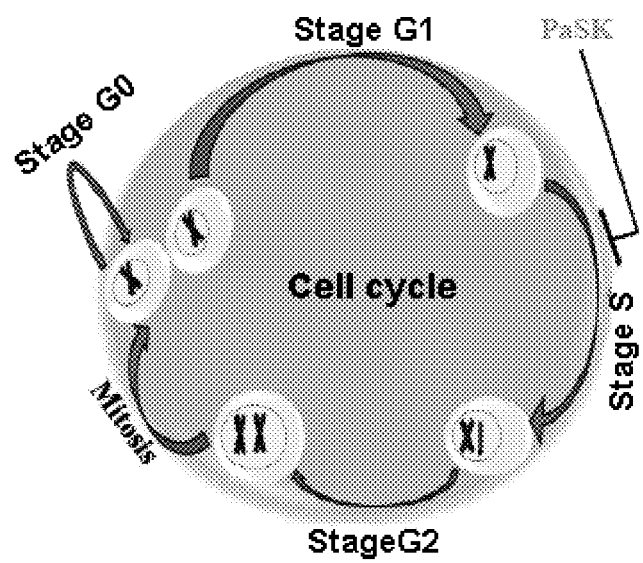

FIGS. 11A and 11B show the graphs with the cell distribution found in each stage of the cell cycle obtained by flow cytometry, detecting fluorescence of propidium iodide. For the control cells and in cells treated with PaSK the following distribution was observed: in stage G1 52.0% and 57.9%, in stage S 40.0% and 33.2%, and in stage G2 8.0% and 9.0%, respectively.

FIG. 11C shows the percentage of cells in each stage of cell cycle, G1, S and G2, and the standard deviations (SD) of the two replicates analysed for the treatments with PaSK and for the control cells. A comparison was made to see if there were statistically significant differences in each stage of the cycle between the control cells and the cells treated with the peptide used in the two-tailed Student's t-test. FIG. 11D is a schematic representation of the cell cycle showing the stage affected by the action of the peptide PaSK.

The peptide PaSK shows antiproliferative activity, as the treated cells present a statistically significant reduction in the percentage of cells in stage S and an increase in stage G1, although the latter lacks statistical significance (FIGS. 11C and 11D).

Example 5. Differential Proteomic Analysis in Triple-Negative Breast Cancer Cells Treated with the Peptide PaSK A differential proteomic analysis was performed by SWATH to determine the molecular mechanisms by which the peptide exerts antiproliferative activity against triple-negative breast cancer cells MDA-MB-231 without killing the cells.

Figure 12:
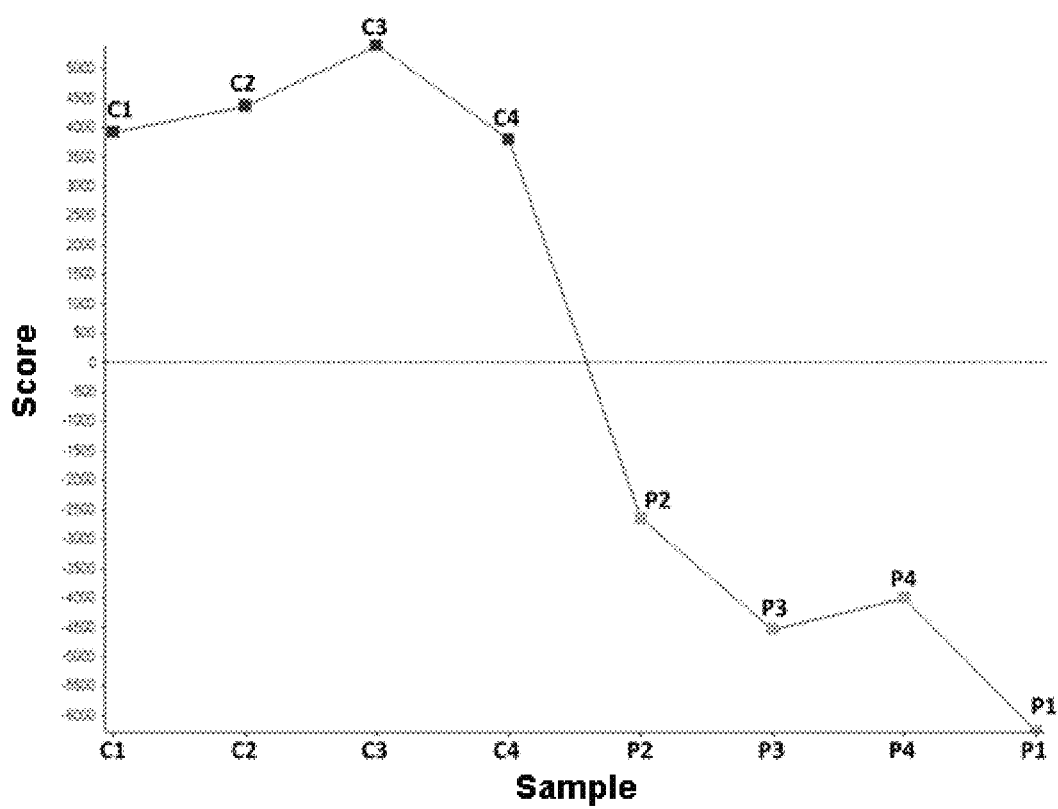
FIG. 12. Discriminant analysis of the quantitative measures of proteins obtained in the control and treatment replicates of the differential proteomic analysis with the software Marker View 1.3. 8 samples were analysed (4 replicates of the control (samples C1-C4) and 4 replicates of the treatment with PaSK (samples P1-P4)).

Eight samples were analysed (4 replicates of the control and 4 replicates of the treatment with PaSK) identifying a total of 1,571 proteins (FDR 1%). With the quantitative data a discriminant analysis was conducted using the software Marker View 1.3, obtaining two clearly differentiated group, that of the control replicates and that of the treatment replicates (FIG. 12).

A Student's t-test (p≤0.05) was conducted for the two conditions (control and treatment) and 31 out of the 1,571 total quantified proteins (FDR 1%) were expressed differentially. Of these, 24 reduced their abundance and 7 increased in the treatment compared to the control (not shaded and shaded, respectively, in Table 1).

TABLE 1

Protein differential expression in MDA-MB-231 cells treated and not treated with the peptide PaSK. In the treated samples, compared to the control samples, the unshaded and shaded proteins respectively reduced and increased their abundance (Student's t-test, p ≤ 0.05). T indicates treated samples, C indicates control samples.

| Peak name | Group | t-value | p-value | T/C change ratio |
|---|---|---|---|---|
| sp\|O43681\|ASNA__HUMAN | ATPase ASNA1 | 3.928518034 | 0.02483 | 0.21 |
| sp\|P06132\|DCUP__HUMAN | Uroporfphyrinogen decarboxylase | 4.993985482 | 0.00485 | 0.21 |
| sp\|Q9H2U1\|DHX36__HUMAN | DHX36 ATP-dependent RNA helicase | 2.904876045 | 0.02776 | 0.27 |
| sp\|Q6PKG0\|LARP1__HUMAN | La related protein 1 (LARP1) | 3.781059497 | 0.00944 | 0.28 |
| sp\|Q9NR46\|SHLB2__HUMAN | Endophilin-B2 | 4.204194474 | 0.00903 | 0.29 |
| sp\|O43583\|DENR__HUMAN | Density regulated protein | 2.881733444 | 0.02873 | 0.31 |
| sp\|P26368\|U2AF2__HUMAN | U2AF union factor 65 kDa subunit | 2.827938614 | 0.03412 | 0.31 |
| sp\|Q9UIG0\|BAZ1B__HUMAN | Tyrosine-protein kinase BAZ1B | 4.121548898 | 0.00622 | 0.31 |
| sp\|Q92544\|TM9S4__HUMAN | Member 4 of the transmembrane 9 superfamily | 4.361795167 | 0.01640 | 0.37 |
| sp\|P28340\|DPOD1__HUMAN | DNA polymerase delta catalytic subunit | 2.992215607 | 0.04858 | 0.50 |
| sp\|P54819\|KAD2__HUMAN | Adenylate kinase 2, mitochondrial | 2.880711379 | 0.02808 | 0.51 |
| sp\|P46777\|RL5__HUMAN | 60 S ribosomal protein L5 (RPSL5) | 2.540854614 | 0.04416 | 0.60 |
| sp\|Q99961\|SH3G1__HUMAN | Endophilin-A2 | 3.829746938 | 0.01530 | 0.63 |
| sp\|P55145\|MANF__HUMAN | Mesencephalic astrocyte-derived neurotrophic factor | 2.878103845 | 0.04330 | 0.63 |
| sp\|Q05682\|CALD1__HUMAN | Caldesmon | 2.767832865 | 0.03276 | 0.71 |
| sp\|P67936\|TPM4__HUMAN | Tropomyosin alpha-4 chain | 2.828936100 | 0.03159 | 0.74 |
| sp\|P37802\|TAGL2__HUMAN | Transgelin-2 | 3.767777780 | 0.00985 | 0.75 |
| sp\|P51114\|FXR1__HUMAN | Fragile X mental retardation protein 1 | 2.578347605 | 0.04190 | 0.76 |
| sp\|P62277\|RS13__HUMAN | 40S ribosomal protein S13 (RPS13) | 2.983650325 | 0.02454 | 0.82 |
| sp\|P17812\|PYRG1__HUMAN | CTP synthase 1 | 3.226835542 | 0.03034 | 0.82 |
| sp\|Q9H3H3\|CK068__HUMAN | UPF0696 protein C11orf68 | 5.038964701 | 0.00243 | 0.83 |
| sp\|P55884\|EIF3B__HUMAN | Eukaryotic translation initiation factor 3B (EIF3B) | 2.849369384 | 0.03000 | 0.84 |
| sp\|Q92841\|DDX17__HUMAN | Probable DDX17 ATP-dependent RNA helicase | 3.097817756 | 0.04655 | 0.84 |
| sp\|Q01105\|SET__HUMAN | SET protein | 2.811921013 | 0.04233 | 0.90 |
| sp\|Q9H5V8\|CDCP1__HUMAN | Protein 1 containing domain CUB | −3.095597963 | 0.03259 | 1.22 |
| sp\|Q9Y6N5\|SQRD__HUMAN | Sulphide: quinone oxidoreductase (SQRDL), mitochondrial | −2.721378907 | 0.03583 | 1.30 |
| sp\|O00560\|SDCB1__HUMAN | Sintenin-1 | −2.958446255 | 0.03792 | 1.43 |
| sp\|P15153\|RAC2__HUMAN | Ras-related C3 botulinum toxin substrate 2 | −3.383777979 | 0.01906 | 1.45 |
| sp\|Q16881\|TRXR1__HUMAN | Thioredoxin reductase 1 (TXNRD1), cytoplasmic | −2.833271929 | 0.03590 | 1.59 |
| sp\|P50281\|MMP14__HUMAN | Matrix metalloprotease-14 | −3.227397623 | 0.03678 | 1.92 |
| sp\|P07203\|GPX1__HUMAN | Glutathione peroxidase 1 (GPX1) | −5.481709009 | 0.00695 | 5.89 |

Figure 13:
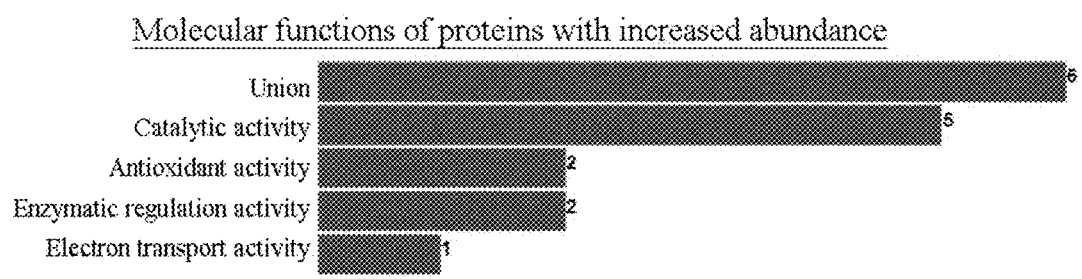
FIG. 13. Differential protein clusters by molecular function. Clusters of proteins with reduced abundance (A) and increased abundance (B) in the treatment/control ratio. Performed in Uniprot.
Figure 13:
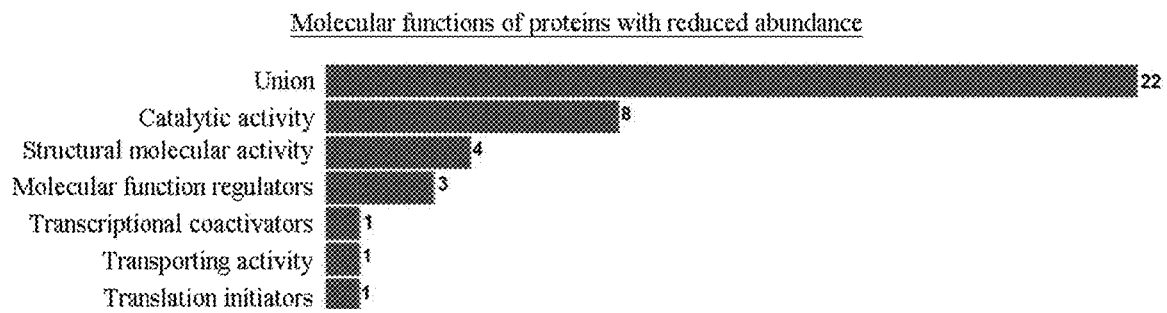

In addition, the differential proteins were grouped into functional clusters in Uniprot, where the clusters were shown in a descriptive manner for both proteins with reduced abundance and increased abundance in the treatment/control ratio. FIG. 13 shows the distribution by molecular function. Among proteins with reduced abundance, the majority of functions correspond to binding proteins (91.7%), which show catalytic activity (33.3%), with structural molecular activity (16.7%), molecular function regulators (12.5%) and, finally, transcriptional coactivators, transporters and translation initiators (4.2%) (FIG. 13A). On the other hand, among proteins with increased abundance the majority are also binding proteins (85.7%), those with catalytic activity (71.4%), with antioxidant activity and enzymatic regulation activity, each one (28.6%) and, finally, with electron transport activity (14.3%) (FIG. 13B).

The results of the differential proteomic analysis confirm that the peptide PaSK acts on intracellular targets. Of the 31 proteins with statistically significant differential expression, 24 reduced their expression and 7 increased it in MDA-MB-231 cells treated with the peptide (Table 1). These are proteins with oncogenic capability, some of which have been described as being overexpressed in various types of tumour cells and which are involved, for example, in the transport of vesicles, signal transduction and apoptosis, in the alteration of metabolic pathways, DNA repair, transcription or post-transcriptional regulation and translation processes, cell adhesion and motility related to metastasis and in responses to oxidative stress.

With regard to the regulation of the cell cycle, of the 24 proteins whose expression was reduced in cells treated with PaSK, the eukaryotic translation initiation factor 3B (EIF3B), the ribosomal proteins S13 and L5 (RPS13 and RPSL5, respectively) and the La related protein 1 (LARP1) stand out. EIF3 is a protein complex that organises a network of interactions between several eukarotic transduction initiation factors that are associated in subunit 40S and which participate in the various reactions involved in translation. It also has other regulatory functions, such as reinitiating the translation of polycystronic mRNA and acting as a receptor for kinase proteins controlling protein synthesis. It has been shown that the down-regulation of EIF3B expression causes cell accumulation in the stage G0/G1, significantly reducing the number of tumour cells in stage S, suggesting that EIF3B may be associated with an inhibition of DNA replication that results in a lower cell growth rate.

Ribosomal proteins S13 and L5 form part of subunits 40S and 60S of the ribosome, respectively. It has been previously described that the overexpression of RPS13 in gastric cancer cells promotes growth and transition from stage G1 to stage S of the cell cycle, while when RPS13 is down regulated in said cells the number of cells stopped in stage G1 is increased. It has been described that the loss of RPL5 prevents biogenesis of ribosomes and protein synthesis. This loss does not result in a complete shutdown of the cell cycle, but strongly inhibits its progress. Therefore, the reduction of both EIF3B and RPL5 would induce a control point for the cell cycle independently of p53. These results agree with those obtained in the analysis of the antiproliferative activity of the peptide PaSK in Example 4, which showed a significant reduction in MDA-MB-231 cells in stage S (FIG. 11C), which suggests a cell cycle control independent of p53, since the MDA-MB-231 cells have a mutated, non-functional p53 gene as indicated above.

Three of the proteins with increased abundance in cells treated with the peptide PaSK are glutathione peroxidase 1 (GPX1), thioredoxin reductase 1 (TXNRD1) and sulphide: quinone oxidoreductase (SQRDL). The three proteins are involved in the response to oxidative stress and are generally overexpressed in tumour cells. Since the protection against oxidation activates survival genes and inhibits apoptosis, an overexpression of said proteins could be a response of the MDA-MB-231 cells to the anticarcinogenic activity of the peptide PaSK.

Figure 14:
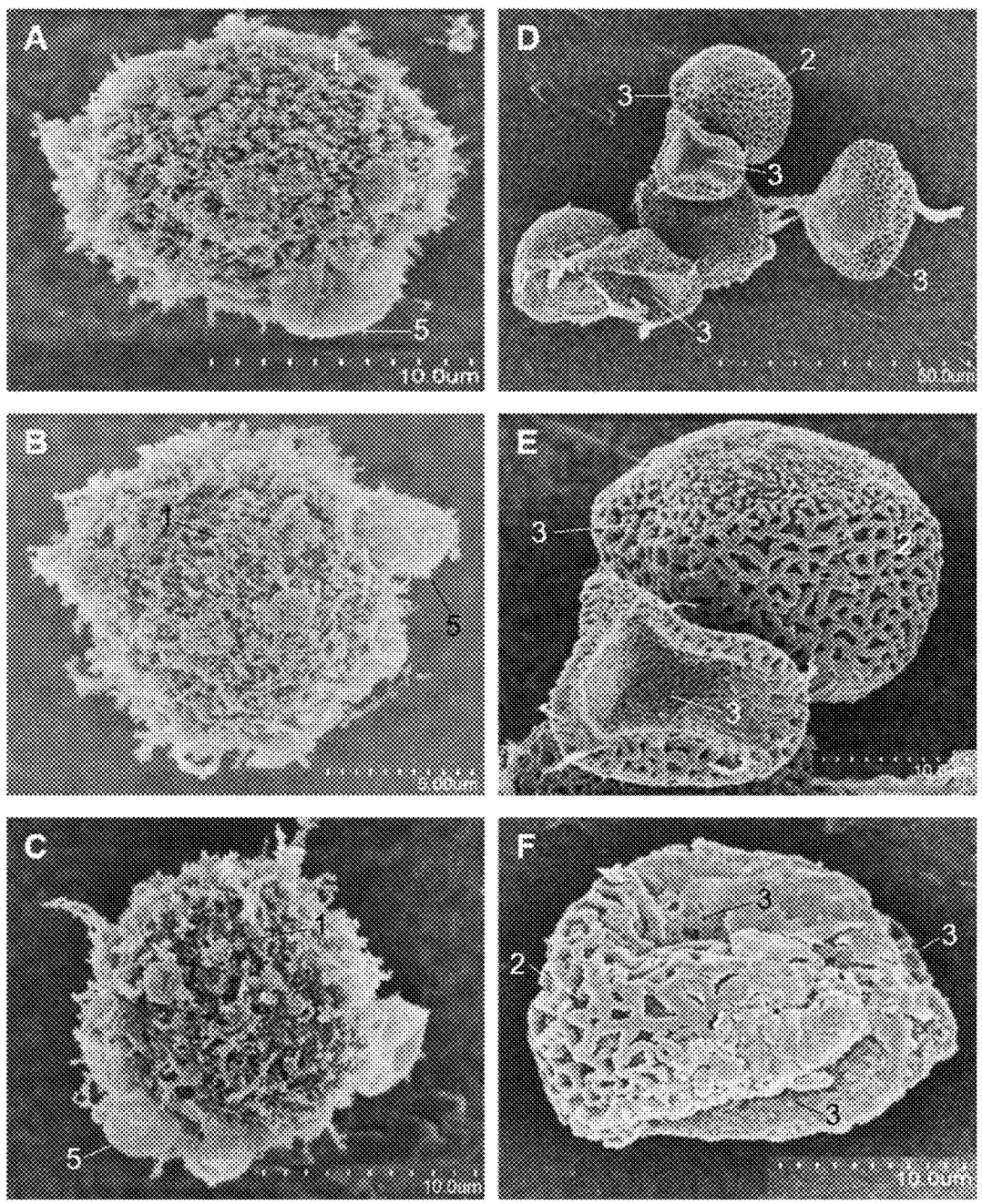
FIG. 14. Images of the damage caused by PaSK in MDA-MB-231 tumour cells obtained by scanning electron microscopy. Cells non-treated with the peptide PaSK (A-B) and treated with PaSK at a concentration of 100 μg/mL for 72 hours (D-F) are shown. The membrane (1) and its expansions (5) in non-treated cells are shown. The membrane of cells treated with PaSK (2) and invaginations and bulges (3) are shown. The number represented in the scale is 10 μm (A), 5 μm (B), 10 μm (C), 50 μm (D), 10 μm (E) and 10 μm (F).
Figure 15:
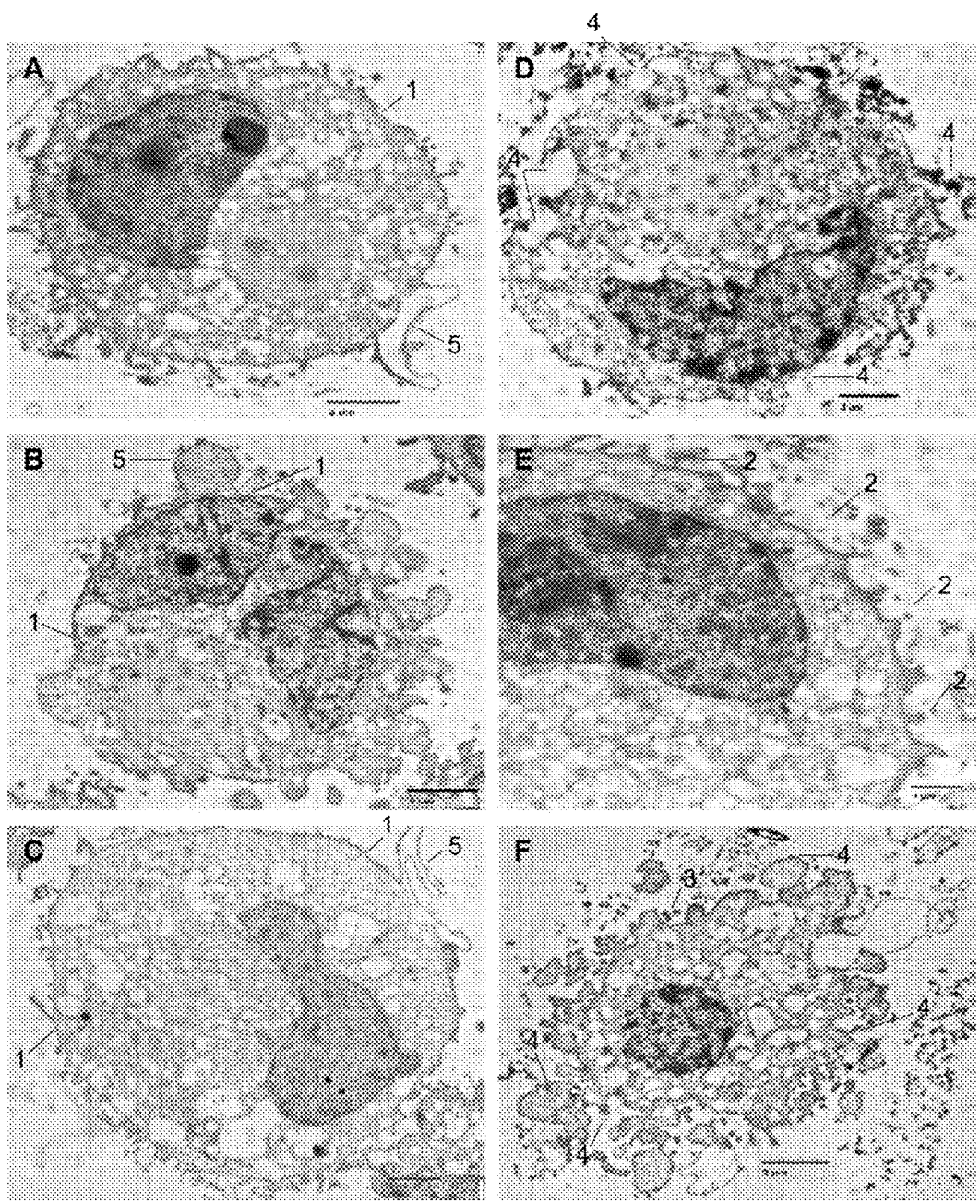
FIG. 15. Images of the damage caused by PaSK in MDA-MB-231 tumour cells obtained by transmission electron microscopy. Cells non-treated with the peptide PaSK (A-B) and treated with PaSK at a concentration of 100 μg/mL for 72 hours (D-F) are shown. The membrane (1) and its expansions (5) in non-treated cells are shown. The membrane of cells treated with PaSK (2), invaginations and bulges (3) and membrane ruptures and vesicles with cytoplasm debris (4) are shown. The number represented in the scale is 2 µm (A), 2 µm (B), 2 µm (C), 2 µm (D), 1 µm (E), 2 µm (F).

Example 6. Effect of the Peptide PaSK on the Morphology of Triple-Negative Breast Cancer Cells Both scanning electron microscopy and transmission electron microscopy provide high resolution images, which were used to view the morphological and ultrastructural changes caused by the peptide PaSK in the membrane and inside of tumour cells. The MDA-MB-231 cells were treated with the peptide PaSK at a concentration of 100 µg/mL for 72 h, and were analysed using scanning electron microscopy (FIG. 14) and transmission electron microscopy (FIG. 15). The images show that the peptide PaSK induced significant morphological changes in the MDA-MB-231 tumour cells. Both scanning electron microscopy and transmission electron microscopy of non-treated cells shows a circular shape with a continuous and intact membrane and the villi typical of human cells (1). However, in cells treated with PaSK an irregular membrane was observed in which the villi appear to be breaking down to form a structure that is disintegrating (2). In addition, highly pronounced invaginations (3) and full breaks of the membrane were observed, which in some cases recircularised to form vesicles with cytoplasm residues (4). Although non-treated cells also showed what appeared to be membrane expansion, the membrane is continuous (5) instead of interrupted as in the treated cells. These results make it clear that the peptide PaSK has a membranolitic action mechanism.

Example 7. Analysis of the Cytotoxic Effect of Combined Treatments with the Peptide PaSK and Chemotherapeutic Agents in Triple-Negative Breast Cancer Cells In this example, the MDA-MB-231 triple-negative breast cancer cells were seeded on a plate with 96 wells, with a density of $7.5 \times 10^3$ cells per well and a volume of 50 µL of the medium DMEM/F-12 supplemented with bovine foetal serum 10%, and allowed to incubate for 24 h at 37° C. in an atmosphere containing 5% $CO_2$ to promote cell adhesion. The treatments with chemotherapeutic agents or combinations with PaSK were performed on a total volume of 100 µL per well with 5% bovine foetal serum to limit the degradation of the peptide due to serum proteases. The cells were incubated at 37° C. for 72 h.

For the MTS tests, 10 µL of MTS solution was added to each well and allowed to incubate for 3 h at 37° C. The absorbance at 490 nm was measured with the equipment Perkin Elmer Wallac 1420 Victor2 Microplate Reader.

The differential proteomic analysis in MDA-MB-231 triple-negative breast cancer cells treated and not treated with the peptide PaSK revealed a significant reduction in the proteins UROD, ASNA1, TM9SF4 and LARP1. It has been described in the state of the art that a reduction of the expression of said proteins increases sensitivity of tumour cells to various chemotherapy agents. To determine whether PaSK sensitises MDA-MB-231 cells to chemotherapy agents, the cytotoxic effect was analysed of combined treatments of the peptide PaSK at a concentration of 100 µg/mL (at which the peptide on its own has a statistically significant cytotoxicity of 3% to 10%), with various concentrations of the chemotherapy agents doxorubicin (0.10, 0.25, 0.50, 1 and 2 μM), paclitaxel (0.0001, 0.001, 0.01, 1, 10, 100 μM), cisplatin (5, 10, 20, 30, 40, 50, 65 and 100 μM) and 5-fluorouracyl (2, 8, 20, 40, 80, 400, 1000 μM), analysing cell viability by the MTS colorimetric technique.

Figure 16:
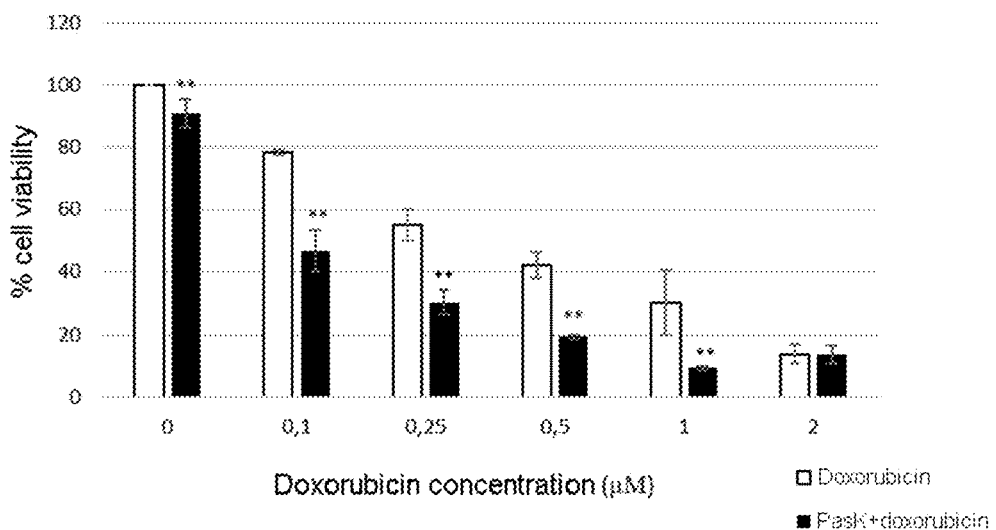
FIG. 16. Cytotoxic effect of combined treatment of the peptide PaSK with doxorubicin, paclitaxel, cisplatin and 5-fluorouracyl in MDA-MB-231 cells. Graphs of cell viability obtained by MTS tests after 72 h of treatment, combining PaSK at a concentration of 100 µg/mL with the various chemotherapy agents. A) Combination with doxorubicin (0.10, 0.25, 0.50, 1 and 2 µM): Means of the 4 replicates with the corresponding standard deviations. B) Combination with paclitaxel (0.0001, 0.001, 0.01, 1, 10, 100 µM): Means of the 4 replicates with the corresponding standard deviations. C) Combination with cisplatin (5, 10, 20, 30, 40, 50, 65 and 100 µM): Means of the 3 replicates with the corresponding standard deviations. D) Combination with 5-fluorouracyl (2, 8, 20, 40, 80, 400, 1000 µM): Means of the 4 replicates with the corresponding standard deviations. Asterisks indicate statistically significant differences between treatments (Student's t-test, $*p \leq 0.05$ and $**p \leq 0.01$).
Figure 16:
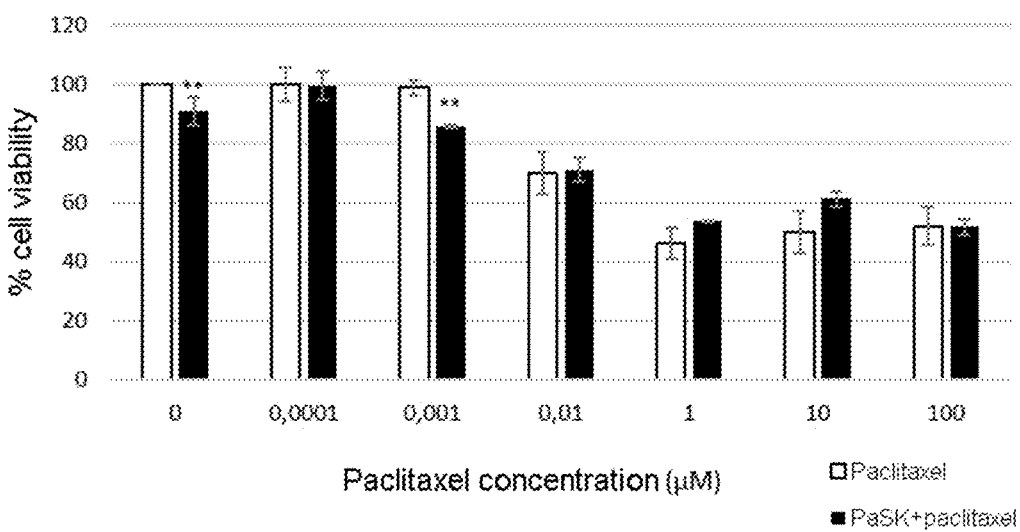
Figure 16:
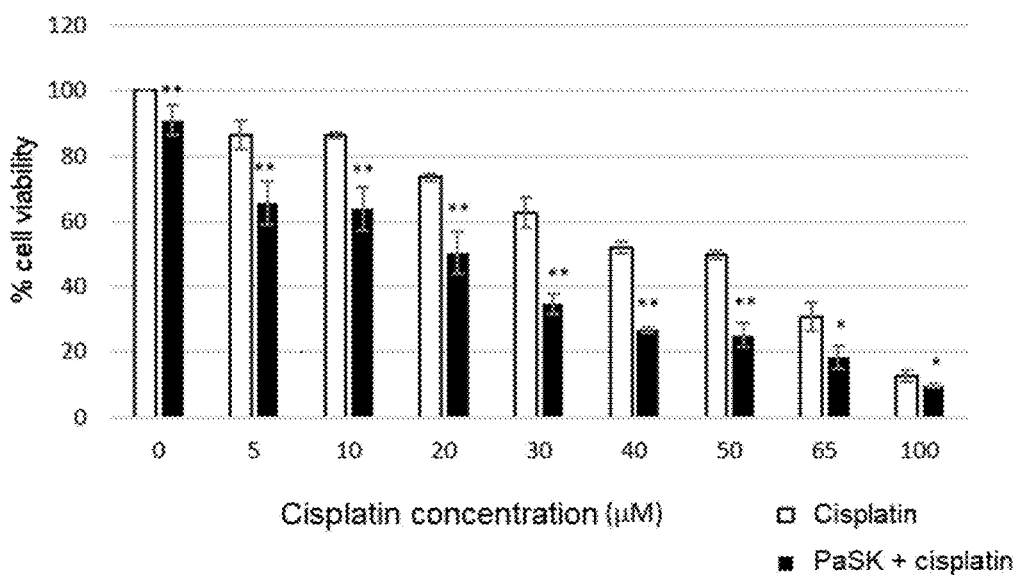
Figure 16:
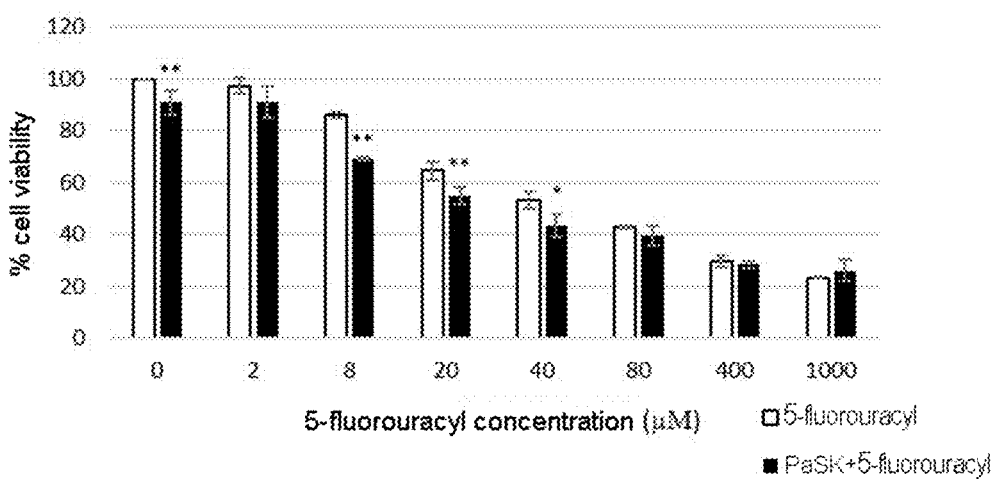

FIG. 16A shows the percentage cell viability obtained and the standard deviations (SD) for the 4 replicates analysed after treating the cells with doxorubicin and with the combination of doxorubicin and PaSK. A statistically significant increase was observed in the cytotoxicity of the combined treatment with doxorubicin and PaSK, with respect to treating the cells only with doxorubicin, for all the concentrations of doxorubicin tested.

FIG. 16B shows the percentage cell viability obtained and the standard deviations (SD) for the 4 replicates analysed after treating the cells with paclitaxel and with the combination of paclitaxel and PaSK. In this case, a statistically significant difference in cytotoxicity was observed only for the combined treatment of paclitaxel and PaSK with respect to treatment with only paclitaxel when the paclitaxel concentration was 0.001 μM.

FIG. 16C shows the percentage cell viability obtained and the standard deviations (SD) for the 3 replicates analysed after treating the cells with cisplatin and with the combination of cisplatin and PaSK. A statistically significant increase was observed in the cytotoxicity of the combined treatment with cisplatin and PaSK, with respect to treating the cells only with cisplatin, for all the concentrations of cisplatin tested.

FIG. 16D shows the percentage cell viability obtained and the standard deviations (SD) for the 4 replicates analysed after treating the cells with 5-fluorouracyl and with the combination of 5-fluorouracyl and PaSK. In this case, a statistically significant difference in cytotoxicity was observed for the combined treatment of 5-fluorouracyl and PaSK with respect to treatment with only 5-fluorouracyl for three concentrations of 5-fluorouracyl (8, 20 and 40 μM).

Figure 17:
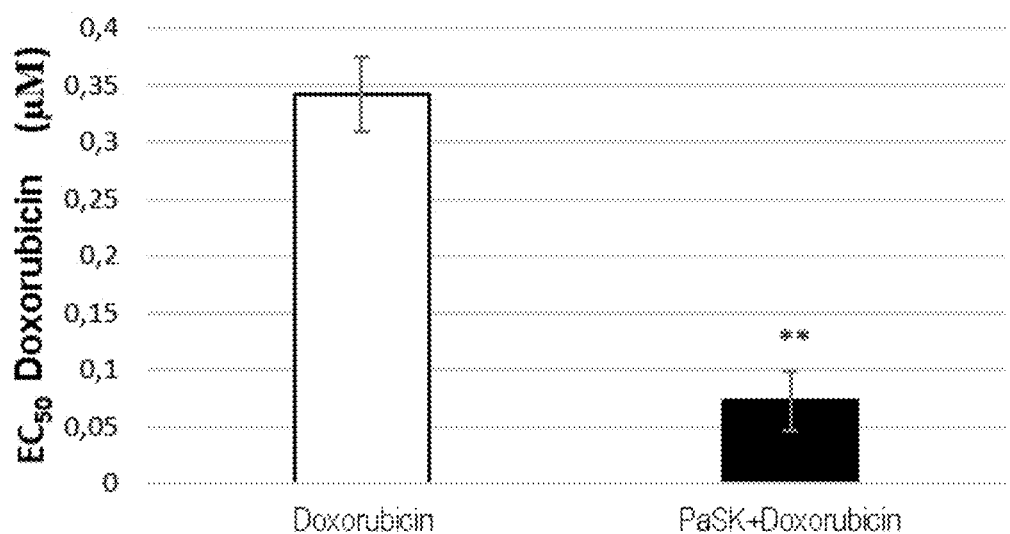
FIG. 17. Comparison of the $EC_{50}$ of MDA-MB-231 cells treated with doxorubicin and cisplatin and combination of both with PaSK. A) $EC_{50}$ of treatment with doxorubicin and combined treatment with doxorubicin and PaSK. B) $EC_{50}$ of treatment with paclitaxel and combined treatment with paclitaxel and PaSK. C) $EC_{50}$ of treatment with cisplatin and combined treatment with cisplatin and PaSK. D) $EC_{50}$ of treatment with 5-Fluorouracyl and combined treatment with 5-Fluorouracyl and PaSK. Means of the 3 replicates with the corresponding standard deviations. Asterisks indicate statistically significant differences in the $EC_{50}$ between treatments (Student's t-test, $*p \leq 0.05$ $**p \leq 0.01$). $EC_{50}$ obtained with online software available from AAT Bioquest (Sunnyvale, Calif., USA).
Figure 17:
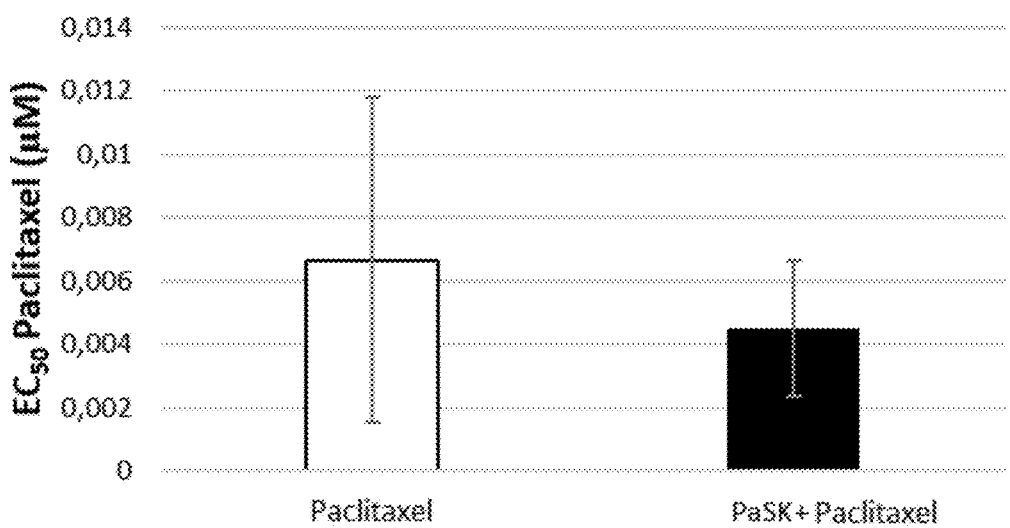
Figure 17:
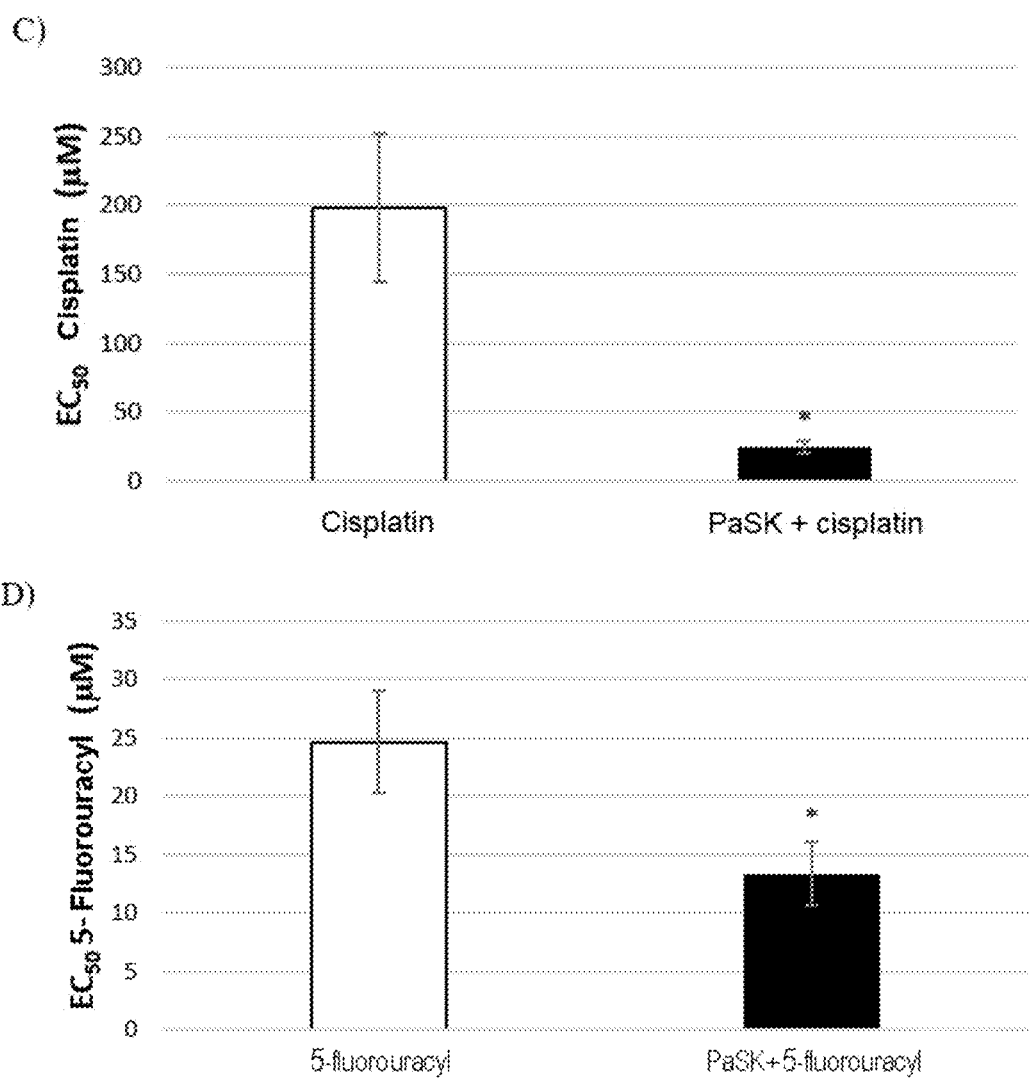

In FIG. 17A, $EC_{50}=0.407\pm0.033$ μM was observed for treatment with doxorubicin, while for treatment with doxorubicin combined with PaSK, $EC_{50}=0.077\pm0.026$ μM was observed. The means of the 3 replicates analysed are shown, as well as their standard deviations (SD), determining that the reduction in $EC_{50}$ for the combined treatment with doxorubicin and PaSK, with respect to treatment with only doxorubicin, is statistically significant.

In FIG. 17B, $EC_{50}=0.008\pm0.005$ μM was observed for treatment with paclitaxel, while for treatment with paclitaxel combined with PaSK, $EC_{50}=0.003\pm0.002$ μM was observed. The means of the 3 replicates analysed are shown, as well as their standard deviations (SD), determining that the reduction in $EC_{50}$ for the combined treatment with paclitaxel and PaSK, with respect to treatment with only paclitaxel, is not statistically significant.

In FIG. 17C, $EC_{50}=168.16\pm53.89$ μM was observed for treatment with cisplatin, while for treatment with cisplatin combined with PaSK $EC_{50}=22.50\pm4.29$ μM was observed. The means of the 3 replicates analysed are shown, as well as their standard deviations (SD), determining that the reduction in $EC_{50}$ for the combined treatment with cisplatin and PaSK, with respect to treatment with only cisplatin, is statistically significant.

Lastly, in FIG. 17D, $EC_{50}=25.34\pm4.33$ μM was observed for treatment with 5-fluorouracyl, while for treatment with 5-fluorouracyl combined with PaSK, $EC_{50}=12.22\pm2.72$ μM was observed. The means of the 3 replicates analysed are shown, as well as their standard deviations (SD), determining that the reduction in $EC_{50}$ for the combined treatment with 5-fluorouracyl and PaSK, with respect to treatment with only 5-fluorouracyl, is statistically significant.

SEQUENCE LISTING FREE TEXT

SEQ ID NO: 1
*Tribolium castaneum* Defensin 3; fragment PaSK
SEQ ID NO: 2
*Tribolium castaneum* Defensin 3; fragment TcDef3-pep

REFERENCES

Contreras, E., Benito-Jardón, M., López-Galiano, M. J., Real, M. D. and Rausell, C. (2015). *Tribolium castaneum* immune defense genes are differentially expressed in response to *Bacillus thuringiensis* toxins sharing common receptor molecules and exhibiting disparate toxicity. Developmental and Comparative Immunology. 50, 139-145.

Rajamuthiah, R. et al. (2015). A defensin from the model beetle *Tribolium castaneum* acts synergistically with telavacin and daptomycin against multidrug resistant *Staphylococcus aureus*. PLOS One. 10(6):1-14.

Tonk, M. et al. (2015). *Tribolium castaneum* defensins are primarily active against Gram– positive bacteria. J Invertebrate Pathol. 132: 208-215.

The invention claimed is:

1. A peptide consisting of the sequence of SEQ ID NO: 1.

2. A pharmaceutical composition comprising the peptide according to claim 1 and at least one pharmaceutically acceptable excipient or carrier.

3. The pharmaceutical composition according to claim 2, wherein said at least one pharmaceutically acceptable excipient or carrier is selected from the group consisting of: organic nanoparticles selected from the group consisting of lipids, nanoemulsions, polymer micelles, SCK nanoparticles, liposomes, nanogels, hydrogels, lipoplexes, and polyplexes; polymers selected from the group consisting of albumin, cellulose, chitosan, alginate, gelatin, poly-c-caprolactone (PCL), hydroxyethyl starch (HES), polyglycolate (PGA), poly-(lactic-co-glycolid), polylactide (PLA), poly(d,l-lactide-co-glycolide) (PLGA), polyethyleneglycol (PEG), N-(2-hydroxypropyl) metacrylamide (PHPMA) and dextrane; dendrimers selected from the group consisting of polyether-hydroxylamine (PEHAM), polyamidoamine (PAMAM), polyesteramine, polypropyleneamine, and polyglycerol; nanofibers selected from the group consisting of carbon nanotubes, nanofibers of poly(d,l-lactide-co-glycolide) (PLGA), nanofibers of polyethyleneglycol (PEG), nanofibers of chitosan, nanofibers of poly(vinyl alcohol) (PVA), nanofibers of polylactide (PLA), nanofibers of polyethylene oxide, and nanofibers of poly-c-caprolactone (PCL); and inorganic nanoparticles selected from the group consisting of: gold nanoparticles, metal oxide nanoparticles, titanium oxide nanoparticles, platinum oxide nanoparticles, superparamagnetic iron oxide nanoparticles (SPIO-NPs), diamond-based nanoparticles, and QD nanoparticles.

4. The pharmaceutical composition according to claim 2, further comprising an antibiotic agent, a chemotherapeutic agent, or an immunotherapeutic agent.

5. The pharmaceutical composition according to claim 4, wherein said antibiotic agent is selected from the group consisting of fusidic acid, arsphenamine, clindamycin, chloramphenicol, ethambutol, fosfomycin, furazolidone, isoniazide, lincomycin, linezolid, metronidazole, mupirocin, nitrofurantoin, pirazinamide, platensimycin, quinupristin, rifampicin, tinidazole, aminoglucosides, ansamycins, carbacefem, carbapenem, cephalosporins, glycopeptides, macrolides, monobactamics, penicillins, polypeptides, quinolones, sulfonamides, and tetracyclines.

6. The pharmaceutical composition according to claim 4, wherein said chemotherapeutic agent is selected from the group consisting of anastrozole, capecitabine, carboplatin, oxaliplatin, ciclophosphamide, cisplatin, docetaxel, doxorubicin, eribulin, fulvestrant, imiquimod, letrozol, paclitaxel, romidepsin, triciribine, exemestane, 5-fluorouracil, and gemcitabine.

7. The pharmaceutical composition according to claim 4, wherein said immunotherapeutic agent is selected from the group consisting of dovitinib, ipilimumab, lapatinib, margetuximab, neratinib, nivolumab, olaparib, palbociclib, pembrolizumab, pertuzumab, ruxolitinib, trastuzumab, and veliparib.

8. A method of treating an infection caused by Gram+ bacteria, Gram− bacteria, and/or fungi, said method comprising administering to a subject in need thereof the peptide of claim 1 or a pharmaceutical composition thereof and an antibiotic agent, or administering the peptide of claim 1 or the pharmaceutical composition thereof in combination with an antibiotic.

9. The method according to claim 8, wherein said Gram+ bacterium is *Staphylococcus aureus*.

10. The method according to claim 8, wherein said Gram− bacterium is *Escherichia coli*.

11. The method according to claim 8, wherein said fungus is *Candida albicans*.

12. The method according to claim 8, wherein said antibiotic agent is selected from the group consisting of fusidic acid, arsphenamine, clindamycin, chloramphenicol, ethambutol, fosfomycin, furazolidone, isoniazide, lincomycin, linezolid, metronidazole, mupirocin, nitrofurantoin, pirazinamide, platensimycin, quinupristin, rifampicin, tinidazole, aminoglucosides, ansamycins, carbacefem, carbapenem, cephalosporins, glycopeptides, macrolides, monobactamics, penicillins, polypeptides, quinolones, sulfonamides, and tetracyclines.

13. A method of treating cancer, said method comprising administering a peptide consisting of the sequence of SEQ ID NO: 1 or a pharmaceutical composition containing the same to a subject in need of said treatment.

14. The method according to claim 13, wherein the cancer is selected from the group consisting of breast cancer, anti-HER2 therapy resistant breast cancer, breast carcinoma, breast adenocarcinoma, gastric carcinoma, gastric adenocarcinoma, colon carcinoma, colon adenocarcinoma, pancreatic carcinoma, pancreatic adenocarcinoma, renal cell carcinoma, clear-cell renal cell carcinoma, ovarian carcinoma, ovarian adenocarcinoma, endometrial carcinoma, uterine cervix carcinoma, pulmonary carcinoma, pulmonary adenocarcinoma, non-microcytic lung cancer, small-cell lung cancer, thyroid carcinoma, metastasic papillary thyroid carcinoma, thyroid follicular carcinoma, vesical carcinoma, transitional cell carcinoma of the bladder, prostate gland carcinoma, central nervous system glyal lineage cancer (glyoma), sarcomas, fibrosarcoma, malign fibrous histiocytoma, human Edwing's sarcoma, endometrial stroma sarcoma, osteosarcoma, rabdomiosarcoma, melanoma, embryonary cancers, neuroblastoma, medulloblastoma, retinoblastoma, nephroblastoma, hepatoblastoma, haematological cancers, B-cell leukaemia, T-cell leukaemia, non-Hodgkin's lymphoma, B-cell non-Hodgkin's lymphoma, T-cell non-Hodgkin's lymphoma, Burkitt's lymphoma, Hodgkin's lymphoma, leukaemias, B-cell lymphoma, T-cell lymphoma, and multiple myeloma.

15. The method according to claim 14, wherein the cancer is breast cancer.

16. The method according to claim 15, wherein the breast cancer is triple-negative breast cancer.

17. The method according to claim 13, wherein administering the peptide consisting of SEQ ID NO: 1 or the pharmaceutical composition thereof is in combination with a chemotherapeutic agent or wherein the pharmaceutical composition containing the peptide consisting of the sequence of SEQ ID NO: 1 further comprises a chemotherapeutic agent.

18. The method according to claim 17, wherein said chemotherapeutic agent is selected from the group consisting of anastrozole, capecitabine, carboplatin, oxaliplatin, ciclophosphamide, cisplatin, docetaxel, doxorubicin, eribulin, fulvestrant, imiquimod, letrozol, paclitaxel, romidepsin, triciribine, exemestane, 5-fluorouracil, and gemcitabine.

19. The method according to claim 13 wherein administering the peptide consisting of SEQ ID NO: 1 or the pharmaceutical composition thereof is in combination with an immunotherapeutic agent or wherein the pharmaceutical composition containing the peptide consisting of the sequence of SEQ ID NO: 1 further comprises an immunotherapeutic agent.

20. The method according to claim 19, wherein said immunotherapeutic agent is selected from the group consisting of dovitinib, ipilimumab, lapatinib, margetuximab, neratinib, nivolumab, olaparib, palbociclib, pembrolizumab, pertuzumab, ruxolitinib, trastuzumab, and veliparib.

21. The method according to claim 13, wherein administering the peptide consisting of the sequence of SEQ ID NO: 1 or the pharmaceutical composition containing the same is in combination with a radiotherapeutic treatment.

* * * * *

UNITED STATES PATENT AND TRADEMARK OFFICE
CERTIFICATE OF CORRECTION

PATENT NO. : 11,365,227 B2
APPLICATION NO. : 16/955370
DATED : June 21, 2022
INVENTOR(S) : Maria Dolores Real Garcia et al.

It is certified that error appears in the above-identified patent and that said Letters Patent is hereby corrected as shown below:

In the Claims

Column 23, Claim 3, Line 29 should read:
– albumin, cellulose, chitosan, alginate, gelatin, poly-ε-capro –

Column 23, Claim 3, Line 32 should read:
– l-lactide-co-glycolide) (PLGA), polyethyleneglycol (PEG) –

Column 23, Claim 3, Line 38 should read:
– nanotubes, nanofibers of poly(d,l-lactide-co-glycolide) –

Column 23, Claim 3, Line 42 should read:
– oxide, and nanofibers of poly-ε-caprolactone (PCL); and –

Signed and Sealed this
Twentieth Day of December, 2022

Katherine Kelly Vidal
*Director of the United States Patent and Trademark Office*